(12) United States Patent
Wang et al.

(10) Patent No.: US 8,383,843 B2
(45) Date of Patent: Feb. 26, 2013

(54) METHOD FOR PREPARING A COUMARIN COMPOUND, CHROMENE COMPOUND, AND METHOD FOR PREPARING A CHROMENE COMPOUND

(75) Inventors: Eng-Chi Wang, Kaohsiung (TW); Jui-Chi Tsai, Taipei (TW); Sie-Rong Li, Taipei County (TW); Po-Yuan Chen, Kaohsiung County (TW)

(73) Assignee: Kaohsiung Medical University, Kaohsiung (TW)

( * ) Notice: Subject to any disclaimer, the term of this patent is extended or adjusted under 35 U.S.C. 154(b) by 42 days.

(21) Appl. No.: 12/901,647

(22) Filed: Oct. 11, 2010

(65) Prior Publication Data
US 2012/0088923 A1    Apr. 12, 2012

(51) Int. Cl.
*C07D 311/00* (2006.01)
(52) U.S. Cl. .................. 549/399; 549/404
(58) Field of Classification Search .......... 549/399, 549/404
See application file for complete search history.

(56) References Cited

PUBLICATIONS

Tsai et al. J. Org. Chem., 2009, 74 (22), pp. 8798-8801.*

* cited by examiner

*Primary Examiner* — Nizal Chandrakumar

(74) *Attorney, Agent, or Firm* — Fox Rothschild, LLP; Robert J. Sacco

(57) ABSTRACT

Disclosed herein is a method for preparing a coumarin compound of formula (F), in which $R^1$, $R^2$, and $R^3$ are independently H, $C_1$~$C_7$ alkoxy, $C_1$~$C_7$ alkyl, phenoxy, benzyloxy, or a halogen atom; $R^4$ is an alkyl group; and Ar is an optionally substituted aryl group,

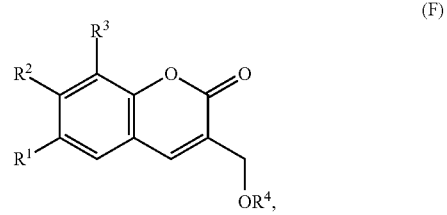

(F)

the method including: treating a chromene compound having the following formula (E)

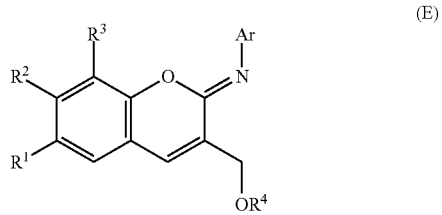

(E)

with an acid in the presence of water.
A chromene compound of formula (E) and a method for preparing the chromene compound of formula (E) are also disclosed.

7 Claims, No Drawings

METHOD FOR PREPARING A COUMARIN COMPOUND, CHROMENE COMPOUND, AND METHOD FOR PREPARING A CHROMENE COMPOUND

BACKGROUND OF THE INVENTION

1. Field of the Invention

This invention relates to a method for preparing a coumarin compound, a chromene compound, and a method for preparing the chromene compound.

2. Description of the Related Art

Coumarins and derivatives thereof have biological activities including anti-carcinogenic activity, fungicidal activity, anti-coagulant activity, etc. For example, coumarin-3-(N-aryl) sulfonamides (see the following formula (I)) exhibit anticancer activity (see N. S. Reddy et al., *Bioorg. Med. Chem. Lett.* 14 (2004) 4093-4097 and Coumarin-3 (N-aryl) carboxamides (see the following formula (II)) can be used to arrest growth of breast cancer cells (see N. S. Reddy at al., *Bioorg. Med. Chem.* 13 (2005), 3141-3147).

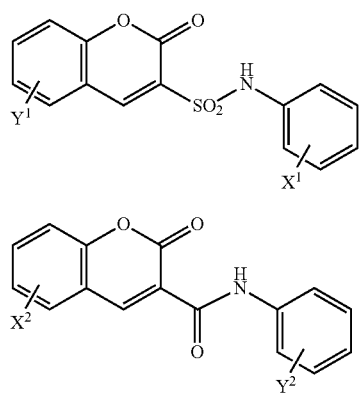

In formula (I), $X^1$ is 4-OCH$_3$, 3-OH, 4-F, or 4-Br; and $Y^1$ is 8-Br, 8-Cl, 8-OCH$_3$, 8-OC$_2$H$_5$; in formula (II), $X^2$ is H, 8-C$_2$H$_5$O, 6-Br, or 6-Cl; and $Y^2$ is 4-Br, 4-I, 4-Cl, 3-NO$_2$, or 3-NH$_2$.

Another coumarin derivative known in the art is 3-methoxymethyl coumarin, which can be prepared from 3-chloromethyl coumarin by the following reaction (see *J. Org. Chem.*, 1960, 25 (10), pp 1713-1716):

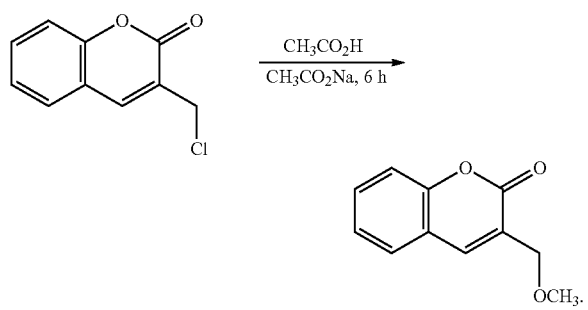

Preparation of 3-methoxymethyl coumarin can also be conducted by the following reaction (see *J. Org. Chem.*, 1962, 27 (2), pp 696-698),

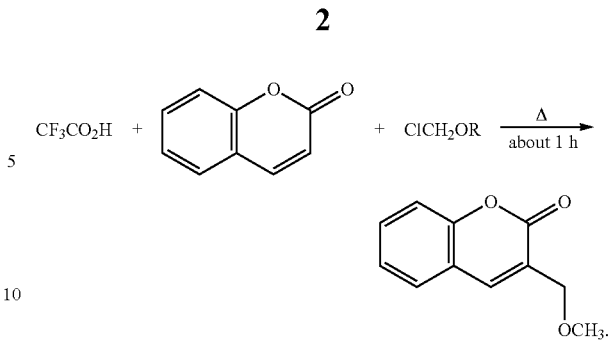

However, trifluoroacetic acid is extremely corrosive and generates a poisonous gas in the reaction, and chloromethyl ether (ClCH$_2$OR) is a carcinogenic substance. Hence, the use of these compounds is likely to result in safety and health concerns.

Therefore, there is a need in the art to develop a process that is simple and safe in the preparation of a coumarin compound.

SUMMARY OF THE INVENTION

The object of the present invention is to provide a method for preparing a coumarin compound, a chromene compound, and a method for preparing the chromene compound.

According to one aspect of this invention, there is provided a method for preparing a coumarin compound of formula (F), in which $R^1$, $R^2$, and $R^3$ are independently H, $C_1$~$C_7$ alkoxy, $C_1$~$C_7$ alkyl, phenoxy, benzyloxy, or a halogen atom; $R^4$ is an alkyl group; and Ar is an optionally substituted aryl group,

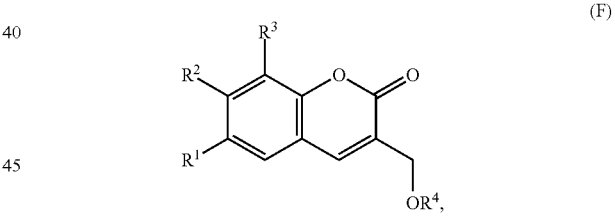

the method comprising: treating a chromene compound having the following formula (E)

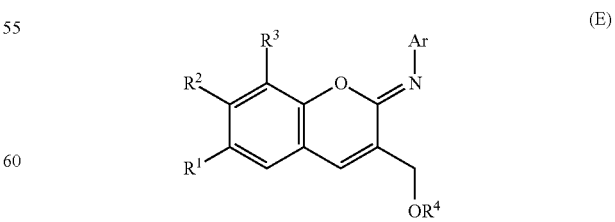

with an acid in the presence of water.

According to another aspect of this invention, there is provided a chromene compound of formula (E):

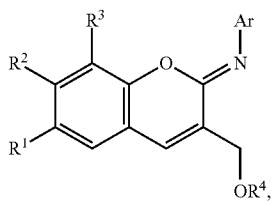

wherein $R^1$, $R^2$, $R^3$, $R^4$, Ar have the same definitions as the aforesaid $R^1$, $R^2$, $R^3$, $R^4$, and Ar.

According to yet another aspect of this invention, there is provided a method for preparing the aforesaid chromene compound of formula (E), including reacting 3-cyano-chromene of formula (B):

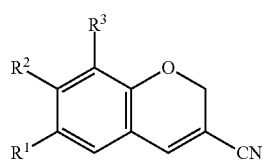

with $R^4$OX and ArNH$_2$ in she presence of a solvent, wherein, $R^1$, $R^2$, and $R^3$ in formula (B), $R^4$ in $R^4$OX, and Ar in ArNH$_2$ have the same definitions as $R^1$, $R^2$, $R^3$, $R^4$, and Ar in formula (E); and X in $R^4$OX is Na or K.

DETAILED DESCRIPTION OF THE PREFERRED EMBODIMENTS

In this invention, the applicants endeavored to develop a simple and safe strategy for the synthesis of a coumarin compound.

Accordingly, this invention provides a chromene compound of formula (E):

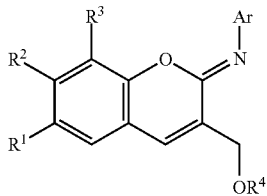

wherein $R^1$, $R^2$, and $R^3$ are independently H, $C_1$~$C_7$ alkoxy, $C_1$~$C_7$ alkyl, phenoxy, benzyloxy, or a halogen atom; $R^4$ is an alkyl group; and Ar is an optionally substituted aryl group.

According to the preferred embodiments of this invention, $R^1$, $R^2$ and $R^3$ are independently H, Cl, Br, benzyloxy (OBn), or methoxy (OMe).

Preferably, $R^4$ is a $C_1$-$C_4$ alkyl group. In the examples of this invention, $R^4$ is methyl (Me), ethyl (Et), i-propyl (i-Pr), or n-butyl (n-Bu).

Preferably, Ar is unsubstituted aryl, haloaryl alkylaryl, or alkoxyaryl. Examples of the unsubstituted aryl include, but are not limited to, phenyl (Ph) and naphthyl. Haloaryl is preferably halophenyl, and examples thereof include, but are not limited to, 4-fluoro-phenyl(4-FPh), 4-chloro-phenyl (4-ClPh), 4-bromo-phenyl (4-BrPh), 3-chloro-phenyl (3-ClPh), and 3-bromo-phenyl (3-BrPh). Alkylaryl is preferably alkylphenyl and examples thereof include, but are not limited to, 4-methyl-phenyl (4-MePh), 3-methyl-phenyl (3-MePh), 2-methyl-phenyl (2-MePh), 5-methyl-phenyl (5-MePh), and 6-methyl-phenyl (6-MePh). Alkoxyaryl is preferably alkoxyphenyl and examples thereof include, but are not limited to, 4-methoxy-phenyl (4-OMePh), 3-methoxy-phenyl (3-OMePh), 2-methoxy-phenyl (2-OMePh), 5-methoxy-phenyl (5-OMePh), and 6-methoxy-phenyl (6-OMePh). In the examples of this invention, Ar is phenyl, 4-fluoro-phenyl, 4-chloro-phenyl, 4-bromo-phenyl, 4-methyl-phenyl, 4-methoxy-phenyl, or 3-methoxy-phenyl.

The compound of formula (E) can be reacted with an acid in the presence of water so as to prepare a coumarin compound of formula (F):

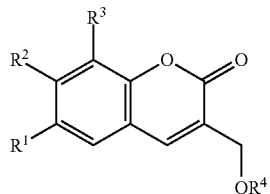

wherein $R^1$, $R^2$, $R^3$, and $R^4$ in formula (F) have the same definitions as $R^1$, $R^2$, $R^3$, and $R^4$ in formula (E).

The acid and water used in the method for preparing the coumarin compound of formula (F) can provide $H_3O^+$ to convert C=N—Ar into C=O. Examples of the acid include HCl, HBr, HI, $CH_3CO_2H$, and combinations thereof. In one preferred embodiment of this invention, the acid is HCl.

Preferably, the chromene compound of formula (E) is prepared by reacting 3-cyanochromene represented formula (B) with $R^4$OX and ArNH$_2$ in the presence of a solvent,

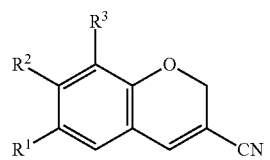

wherein $R^1$, $R^2$, $R^3$, $R^4$ and Ar are as defined above; and X is Na or K.

Preferably, the solvent used for preparing the chromene compound of formula (E) is selected from the group consisting of $R^5$OH and tetrahydrofuran (THF), wherein $R^5$ is $C_1$~$C_4$ alkyl.

Preferably, the reaction in the method for preparing the chromene compound of formula (E) is conducted under a reflux condition.

In the preferred embodiments of this invention, 3-cyano-chromene of formula (B) is 3-cyano-2H-chromene ($B_1$), 6-chloro-3-cyano-2H-chromene ($B_2$), 6-bromo-3-cyano-2H-chromene ($B_3$), 7-benzyloxy-3-cyano-2H-chromene ($B_4$), 7-methoxy-3-cyano-2H-chromene ($B_5$, or 8-methoxy-3-cyano-2H-chromene ($B_6$).

3-cyanochromene of formula (B) may be prepared by conventional techniques. Preferably, 3-cyanochromene is prepared by reacting salicylaldehyde of formula (A) with acrylonitrile in the presence of a catalyst:

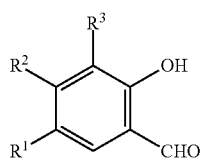

(A)

wherein $R^1$, $R^2$, and $R^3$ are as defined above. In the preferred embodiments of this invention, salicylaldehyde of formula (A) is salicylaldehyde ($A_1$), 5-chlorosalicylaldehyde ($A_2$), 5-chlorosalicylaldehyde ($A_3$), 4-benzyloxysalicylaldehyde ($A_4$), 4-methyloxysalicylaldehyde ($A_5$), or 3-methyloxysalicylaldehyde ($A_6$).

Preferably, the catalyst is 1,4-diazabicyclo[2,2,2]octane (DABCO), 1,8-diazabicyclo[5.4.0]undec-7-ene (DBU), trimethylamine, triethylamine, or triphenylphosphine (TPP).

In the preferred embodiments of this invention, the method for preparing the coumarin compound of formula (F) includes reactions in the following sequence:

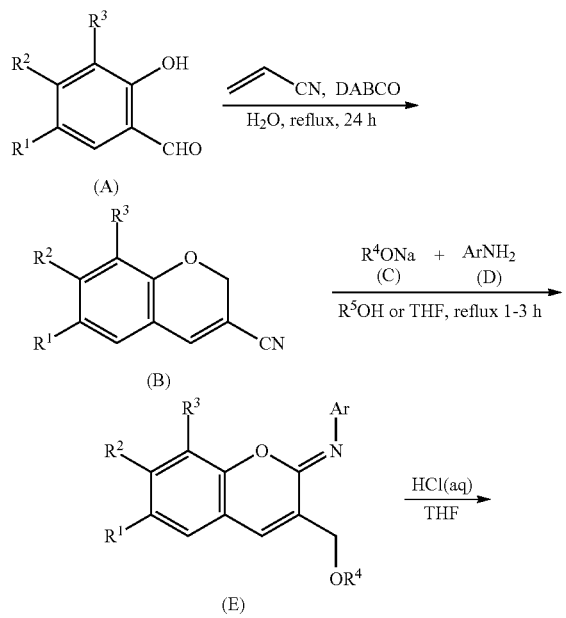

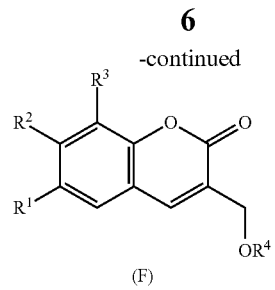

It is noted that $ArNH_2$ (hereinafter referred to as compound (D)) formed as a byproduct of the last reaction can be recycled as the reagent for the reaction of preparing the chromene compound of formula (E). In the aforesaid series of reactions, the reagents and the materials thus used are safe and are commercially available. The coumarin compound of formula (F) can be easily and safely obtained by reacting the chromene compound of formula (E) with an acid.

The following examples are provided to illustrate the merits of the preferred embodiments of the invention, and should not be construed as limiting the scope of the invention.

EXAMPLES

The compounds prepared in the following Examples 1-36 were measured by structure identification using the following general procedures.

General Procedures:
1. The melting point was detected using a micro melting-point apparatus (available from Yanaco company).
2. $^1$H-NMR and $^{13}$C-NMR spectra were detected using a Varian Unity-400 spectrometer.
3. IR spectra were measured in a Perkin Elmer system 2000 FT-IR spectrometer.
4. Elemental analysis was recorded in an element analyzer (trade name: Elementar vario EL III).
5. Mass analysis was measured in a mass spectrometer (trade name: Bruker APEX II).

Before the examples are illustrated, the species of the starting materials of compounds (A), the intermediate chromene compounds (B) and (E), the reagents (C) of $R^4ONa$ and (D) of $ArNH^2$, and the final products of coumarin compounds (F), as well as the substituted groups of $R^1$, $R^2$, $R^3$, and $R^4$ in Examples 1-36 are listed in Table 1 for the sake of clarity.

TABLE 1

| Ex No. | Target compound | Reactants A | B | C | D | E | $R^1$ | $R^2$ | $R^3$ | $R^4$ | Ar |
|---|---|---|---|---|---|---|---|---|---|---|---|
| 1 | $E_1$ | $A_1$ | $B_1$ | $C_1$ | $D_1$ | — | H | H | H | Me | Ph |
| 2 | $E_2$ | | | $C_2$ | $D_1$ | — | H | H | H | Et | Ph |
| 3 | $E_3$ | | | $C_2$ | $D_2$ | — | H | H | H | Et | 4-FPh |
| 4 | $E_4$ | | | $C_2$ | $D_3$ | — | H | H | H | Et | 4-ClPh |
| 5 | $E_5$ | | | $C_2$ | $D_4$ | — | H | H | H | Et | 4-BrPh |
| 6 | $E_6$ | | | $C_2$ | $D_5$ | — | H | H | H | Et | 4-MePh |
| 7 | $E_7$ | | | $C_2$ | $D_6$ | — | H | H | H | Et | 4-OMePh |
| 8 | $E_8$ | | | $C_2$ | $D_7$ | — | H | H | H | Et | 3-OMePh |
| 9 | $E_9$ | | | $C_3$ | $D_1$ | — | H | H | H | i-Pr | Ph |
| 10 | $E_{10}$ | | | $C_4$ | $D_1$ | — | H | H | H | n-Bu | Ph |
| 11 | $E_{11}$ | $A_2$ | $B_2$ | $C_2$ | $D_1$ | — | Cl | H | H | Et | Ph |
| 12 | $E_{12}$ | | | $C_2$ | $D_2$ | — | Cl | H | H | Et | 4-FPh |
| 13 | $E_{13}$ | | | $C_2$ | $D_3$ | — | Cl | H | H | Et | 4-ClPh |
| 14 | $E_{14}$ | | | $C_2$ | $D_4$ | — | Cl | H | H | Et | 4-BrPh |
| 15 | $E_{15}$ | | | $C_2$ | $D_5$ | — | Cl | H | H | Et | 4-MePh |
| 16 | $E_{16}$ | | | $C_2$ | $D_6$ | — | Cl | H | H | Et | 4-OMePh |
| 17 | $E_{17}$ | | | $C_2$ | $D_7$ | — | Cl | H | H | Et | 3-OMePh |
| 18 | $E_{18}$ | $A_3$ | $B_3$ | $C_2$ | $D_1$ | — | Br | H | H | Et | Ph |

TABLE 1-continued

| Ex No. | Target compound | Reactants A | B | C | D | E | Substituted groups of compound (E) or (F) R¹ | R² | R³ | R⁴ | Ar |
|---|---|---|---|---|---|---|---|---|---|---|---|
| 19 | $E_{19}$ |  |  | $C_2$ | $D_2$ | — | Br | H | H | Et | 4-FPh |
| 20 | $E_{20}$ |  |  | $C_2$ | $D_3$ | — | Br | H | H | Et | 4-ClPh |
| 21 | $E_{21}$ |  |  | $C_2$ | $D_4$ | — | Br | H | H | Et | 4-BrPh |
| 22 | $E_{22}$ |  |  | $C_2$ | $D_5$ | — | Br | H | H | Et | 4-MePh |
| 23 | $E_{23}$ |  |  | $C_2$ | $D_6$ | — | Br | H | H | Et | 4-OMePh |
| 24 | $E_{24}$ |  |  | $C_2$ | $D_7$ | — | Br | H | H | Et | 3-OMePh |
| 25 | $E_{25}$ | $A_4$ | $B_4$ | $C_2$ | $D_1$ | — | H | OBn | H | Et | Ph |
| 26 | $E_{26}$ | $A_5$ | $B_5$ | $C_2$ | $D_1$ | — | H | OMe | H | Et | Ph |
| 27 | $E_{27}$ | $A_6$ | $B_6$ | $C_2$ | $D_1$ | — | H | H | OMe | Et | Ph |
| 28 | $F_1$ | $A_1$ | $B_1$ | $C_1$ | $D_1$ | $E_1$ | H | H | H | Me | Ph |
| 29 | $F_2$ | $A_1$ | $B_1$ | $C_2$ | $D_1$ | $E_2$ | H | H | H | Et | Ph |
| 30 | $F_3$ | $A_1$ | $B_1$ | $C_3$ | $D_1$ | $E_9$ | H | H | H | i-Pr | Ph |
| 31 | $F_4$ | $A_1$ | $B_1$ | $C_4$ | $D_1$ | $E_{10}$ | H | H | H | n-Bu | Ph |
| 32 | $F_5$ | $A_2$ | $B_2$ | $C_2$ | $D_1$ | $E_{11}$ | Cl | H | H | Et | Ph |
| 33 | $F_6$ | $A_3$ | $B_3$ | $C_2$ | $D_1$ | $E_{18}$ | Br | H | H | Et | Ph |
| 34 | $F_7$ | $A_4$ | $B_4$ | $C_2$ | $D_1$ | $E_{25}$ | H | OBn | H | Et | Ph |
| 35 | $F_8$ | $A_5$ | $B_5$ | $C_2$ | $D_1$ | $E_{26}$ | H | OMe | H | Et | Ph |
| 36 | $F_9$ | $A_6$ | $B_6$ | $C_2$ | $D_1$ | $E_{27}$ | H | H | OMe | Et | Ph |

Preparation of 3-cyanochromene $(B_1)\sim(B_6)$

Each of the compounds $(B_1)\sim(B_6)$ was prepared according to scheme I below by: mixing 20.0 mmol of a corresponding one of salicylaldehydes $(A_1)\sim(A_6)$ with 30.0 mmol of acrylonitrile to form a mixture; slowly adding a DABCO aqueous solution containing 22.0 mmol of DABCO and 30 mL of water into the mixture to obtain a reaction solution; followed by refluxing the reaction solution under a nitrogen gas environment for 24 hrs.

Scheme I

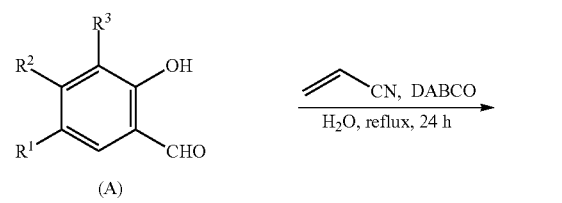

(A)
$(A_1)$: R¹ = H, R² = H, R³ = H
$(A_2)$: R¹ = Cl, R² = H, R³ = H
$(A_3)$: R¹ = Br, R² = H, R³ = H
$(A_4)$: R¹ = H, R² = OBn, R³ = H
$(A_5)$: R¹ = H, R² = OMe, R³ = H
$(A_6)$: R¹ = H, R² = H, R³ = OMe

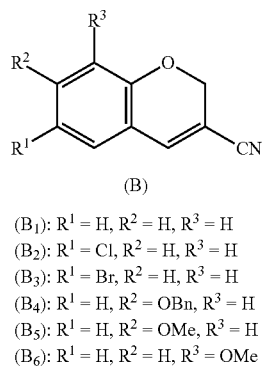

(B)
$(B_1)$: R¹ = H, R² = H, R³ = H
$(B_2)$: R¹ = Cl, R² = H, R³ = H
$(B_3)$: R¹ = Br, R² = H, R³ = H
$(B_4)$: R¹ = H, R² = OBn, R³ = H
$(B_5)$: R¹ = H, R² = OMe, R³ = H
$(B_6)$: R¹ = H, R² = H, R³ = OMe

The reaction product thus formed in the reaction solution was extracted using $CH_2Cl_2$, and was subsequently dried, filtered, concentrated, and purified by column chromatography with a suitable eluent so as to obtain a colorless crystal of 3-cyanochomene of formula (B).

Structure identification of 3-cyanochromenes $[(B_1)\sim(B_6)]$

3-Cyano-2H-chromene $(B_1)$: (2.51 g, 80%); m.p.: 44-45° C.; $R_f$=0.75 (ethyl acetate:n-hexane=1:6); IR (KBr cm⁻¹): 3059, 2851, 2212, 1623, 1482, 1458, 1233, 1211, 1148, 1034, 1020, 898, 759; ¹H-NMR (400 MHz, $CDCl_3$) δ/ppm: 4.81 (2H, d, J=1.6 Hz, H-2), 6.87 (1H, d, 8.0 Hz, ArH), 6.97 (1H, td, J=7.6, 1.2 Hz, ArH), 7.10 (1H, dd, J=8.0, 1.2 Hz, ArH), 7.17 (1H, br s, H-4), 7.27 (1H, m, ArH); ¹³C-NMR (100 MHz, $CDCl_3$) δ/ppm: 64.2, 103.3, 116.4, 116.5, 120.0, 122.4, 128.4, 132.7, 138.8, 154.3; MS (EI) m/z: 157 (M⁺, 92%), 156 (100%).

6-Chloro-3-cyano-2H-chromene $(B_2)$: (2.99 g, 78%); m.p.: 124-126° C.; $R_f$=0.76 (ethyl acetate:n-hexane=1:6); IR (KBr cm⁻¹): 3064, 2917, 2213, 1629, 1479, 1239, 1212, 1019, 914, 816; ¹H-NMR (400 MHz, $CDCl_3$) δ/ppm: 4.83 (2H, d, J=1.6 Hz, H-2), 6.82 (1H, d, J=8.6 Hz, H-8), 7.09 (1H, d, J=2.4 Hz, H-5), 7.11 (1H, br s, H-4), 7.22 (1H, dd, J=8.6, 2.4 Hz, H-7); ¹³C-NMR (100 MHz, $CDCl_3$) δ/ppm: 64.4, 104.8, 115.9, 118.0, 121.1, 127.3, 127.7, 132.3, 137.6, 152.7; MS (EI) m/z: 193 ([M+2]⁺, 29%), 191 (M⁺, 91%), 190 (87%), 156 (100%).

6-Bromo-3-cyano-2H-chromene $(B_3)$: (3.54 g, 75%); m.p.: 132-133° C.; $R_f$=0.77 (ethyl acetate:n-hexane=1:6); IR (KBr cm⁻¹): 3063, 2878, 2211, 1627, 1476, 1236, 1211, 1018, 915, 815; ¹H-NMR (400 MHz, $CDCl_3$) δ/ppm: 4.83 (2H, d, J=1.2 Hz, H-2), 6.76 (1H, d, J=8.4 Hz, H-8), 7.10 (1H, br s, H-4), 7.23 (1H, d, J=2.4 Hz, H-5), 7.36 (1H, dd, J=8.4, 2.4 Hz, H-7); ¹³C-NMR (100 MHz, $CDCl_3$) δ/ppm: 64.4, 104.7, 114.4, 115.9, 118.4, 121.5, 130.6, 135.1, 137.4, 153.2; MS (EI) m/z: 237 ([M+2]⁺, 41%), 235 (M⁺, 49%), 157 (75%), 156 (100%).

7-Benzyloxy-3-cyano-2H-chromene $(B_4)$: (3.79 g, 72%); m.p.: 108-109° C.; $R_f$=0.35 (ethyl acetate:n-hexane=1:9); IR (KBr cm⁻¹): 3033, 2957, 2206, 1615, 1561, 1271, 1166, 851, 737; ¹H-NMR (400 MHz, $CDCl_3$) δ/ppm: 4.77 (2H, d, J=1.2 Hz, H-2), 5.05 (2H, s, $OCH_2Ph$), 6.49 (1H, d, J=2.4 Hz, H-8), 6.59, dd, J=8.6, 2.4 Hz, H-6), 7.01 (1H, d, J=8.6 Hz, H-5), 7.12 (1H, m, H-4), 7.32-7.41 (5H, m, ArH); ¹³C-NMR (100 MHz, $CDCl_3$) δ/ppm: 64.4, 70.2, 99.5, 102.8, 109.6, 113.6, 116.9, 127.4, 128.2, 128.7, 129.6, 136.0, 138.7, 155.9, 162.5; MS (EI) m/z: 263 (M⁺, 7%), 91 (100%); Anal. calcd for $C_{17}H_{13}NO_2$ (263.29): C, (77.55); H, (4.98); N, (5.32). found. C, (77.57); H, (5.02); N, (5.20).

7-Methoxy-3-cyano-2H-chromene ($B_5$): (2.77 g, 74%); m.p.: 97-99° C.; $R_f$=0.30 (ethyl acetate:n-hexane=1:9); IR (KBr cm$^{-1}$): 3065, 2964, 2205, 1618, 1564, 1435, 1279, 868, 805; $^1$H-NMR (400 MHz, CDCl$_3$) δ/ppm: 3.78 (3H, s, OCH$_3$), 4.76 (2H, d, J=0.8 Hz, H-2), 6.40 (1H, d, J=2.4 Hz, H-8), 6.50, (1H, J=8.4, 2.4 Hz, H-6), 7.00 (1H d, J=8.4 Hz, H-5), 7.11 (1H, br s, H-4); $^{13}$C-NMR (100 MHz, CDCl$_3$) δ/ppm: 55.5, 64.4, 99.3, 101.8, 108.9, 113.4, 116.9, 129.5, 138.7, 155.9, 163.4; MS (EI) m/z: 187 (M$^+$, 80%), 186 (100%).

8-Methoxy-3-cyano-2H-chromene ($B_6$): (2.85 g, 76%); m.p.: 105-106° C.; $R_f$=0.58 (ethyl acetate:n-hexane=1:3); IR (KBr cm$^{-1}$): 3056, 2956, 2838, 2210, 1625, 1606, 1575, 1482, 1336, 1274, 1221, 1098, 1021, 733; $^1$H-NMR (400 MHz, CDCl$_3$) δ/ppm: 3.88 (3H, s, OCH$_3$), 4.87 (2H, d, J=1.2 Hz, H-2), 6.75 (1H, dd, J=5.6, 3.6 Hz, ArH), 6.93, (1H, J=3.6 Hz, ArH), 6.93 (1H, d, J=5.6 Hz, ArH), 7.18 (1H, t, J=1.2 Hz, H-4); $^{13}$C-NMR (100 MHz, CDCl$_3$) δ/ppm: 56.1, 64.5, 103.4, 115.2, 116.3, 120.2, 120.7, 122.2, 138.8, 143.2, 148.0; MS (EI) m/z: 187 (M$^+$, 100%), 186 (39%), 144 (69%), 116 (40%), 89 (32%).

Examples 1~27

Preparation of the Chromene Compounds ($E_1$)~($E_{27}$)

Each of the chromene compounds ($E_1$)~($E_{27}$) of Examples 1~27 was prepared according to scheme II below by: dissolving 5.0 mmol of a corresponding one of 3-cyanochromenes ($B_1$)~($B_6$) in THF to form a solution; mixing 7.5 mmol of a corresponding one of the compounds ($C_1$)~($C_4$) and 10.0 mmol of a corresponding one of the compounds ($D_1$)~($D_7$) with the above solution to form a reaction solution; followed by refluxing the reaction solution under a nitrogen gas environment for 1~3 hrs.

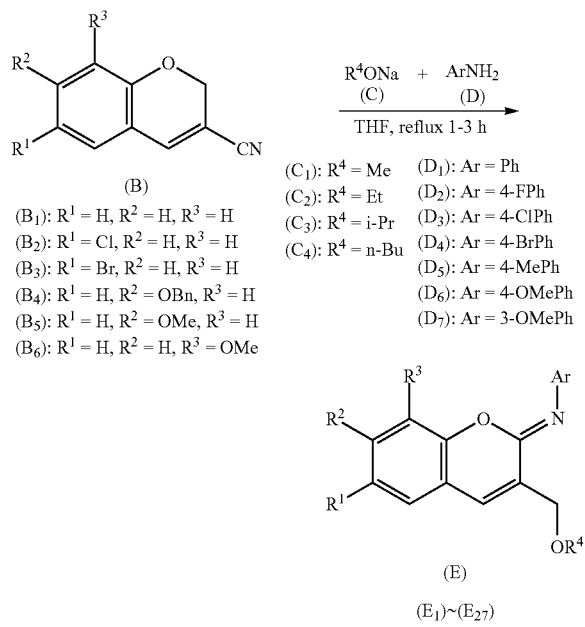

Scheme II

The reaction product thus formed was separated from the reaction solution, and was then purified by column chromatography with a suitable eluent so as to obtain a yellow crystal of intermediate chromene compound of formula (E).

Structure Identification of the Intermediate Chromene Compounds [($E_1$)~($E_{27}$)]

3-Methoxymethyl-2-phenylimino-2H-chromene ($E_1$): (0.86 g, 65%); m.p.: 64-65° C.; $R_f$=0.512 (ethyl acetate:n-hexane=1:7); $^1$H-NMR (CDCl$_3$, 400 MHz) δ/ppm: 3.53 (s, 3H, CH$_2$OCH$_3$), 4.40 (d, J=1.6 Hz, 2H, CH$_2$OCH$_3$), 7.00 (H, J=8.0 Hz, 1H, ArH), 7.06-7.12 (m, 2H, RC=NArH), 1.17 (dt, J=6.4, 1.2 Hz, 2H, RC=NArH), 7.25 (td, J=7.2, 1.6 Hz, 1H, ArH), 7.29 (dd, 7.6, 1.6 Hz, 1H, ArH) 7.32-7.36 (m, 3H, ArH, ArCH=C, RC=NArH); $^{13}$C-NMR (CDCl$_3$, 100 MHz) δ/ppm: 58.98, 69.57, 115.33, 119.79, 122.87, 123.58, 123.69, 127.10, 128.54, 128.90, 129.63, 129.68, 145.95, 147.74, 152.23; IR (KBr cm$^{-1}$): 2936, 2869, 2363, 1644, 1585, 1487, 1451, 1403, 1225, 1180, 1115, 1058, 761, 705; EI-MS (70 eV) m/z: 265 (M$^+$, 10%), 251 (18%), 250 (100%), 235 (27%), 234 (21%), 233 (11%), 232 (22%), 222 (21%); Anal. calcd for $C_{17}H_{15}NO_2$: N, 5.28; C, 76.96; H, 5.70. found: N, 5.22; C, 76.93; H, 5.68.

3-Ethoxymethyl-2-phenylimino-2H-chromene ($E_2$): (1.1 g, 79%); m.p.: 71~72° C.; $R_f$=0.564 (ethyl acetate:n-hexane=1:7); $^1$H-NMR (CDCl$_3$, 400 MHz) δ/ppm: 1.37 (t, J=6.8 Hz, 3H, CH$_2$OCH$_2$CH$_3$), 3.74 (q, J=6.8 Hz, 2H, CH$_2$OCH$_2$CH$_3$), 4.53 (d, J=2.0 Hz, 2H, CH$_2$OCH$_2$CH$_3$), 7.04 (dd, J=8.0, 0.4 Hz, 1H, ArH), 7.11-7.16 (m, 2H, RC=NArH), 7.21-7.24 (m, 2H, RC=NArH), 7.29 (td, J=8.0, 1.2 Hz, 1H, ArH), 7.34-7.41 (m, 3H, ArH, RC=NArH), 7.42 (t, J=1.6 Hz, 1H, ArCH=C); $^{13}$C-NMR (CDCl$_3$, 100 MHz) δ/ppm: 15.58, 67.06, 67.84, 115.69, 120.22, 123.21, 123.92, 124.02, 127.46, 128.90, 129.62, 129.93, 130.02, 146.36, 148.22, 152.57; IR (KBr cm$^{-1}$): 2978, 2861, 2362, 1640, 1583, 1486, 1449, 1386, 1227, 1182, 1116, 1064, 758, 703; EI-MS (70 eV) m/z: 279 (M$^+$, 0.3%), 251 (17%), 250 (100%), 236 (49%), 235 (58%), 233 (47%), 231 (17%), 221 (12%); Anal. calcd for $C_{18}H_{17}NO_2$: N, 5.01; C, 77.40; H, 6.13. found: N, 4.82; C, 77.46; H, 6.21.

3-Ethoxymethyl-2-(4-fluorophenyl)imino-2H-chromene ($E_3$): (0.94 g, 63%); m.p.; 84~86° C., $R_f$=0.538 (ethyl acetate: n-hexane=1:7); $^1$H-NMR (CDCl$_3$, 400 MHz) δ/ppm: 1.35 (t, J=7.2 Hz, 3H, CH$_2$OCH$_2$CH$_3$), 3.72 (q, J=6.8 Hz, 2H, CH$_2$OCH$_2$CH$_3$), 4.49 (d, J=1.6 Hz, 2H, CH$_2$OCH$_2$CH$_3$), 7.02 (dd, J=8.0, 0.8 Hz, 1H, ArH), 7.04-7.07 (m, 2H, RC=NArH), 7.13 (td, J=7.6, 1.2 Hz, 1H, ArH), 7.18-7.22 (m, 2H, RC=NArH), 7.30 (td, 7.6, 1.6 Hz, 1H, ArH), 7.34 (td, J=7.6, 1.2 Hz, 1H, ArH), 7.40 (t, J=1.2 Hz, 1H, ArCH=C); $^{13}$C-NMR (CDCl$_3$, 100 MHz) δ/ppm: 15.23, 66.74, 67.47, 115.07, 115.30, 119.89, 123.72, 124.40, 124.47, 127.20, 129.24, 129.67, 129.77, 152.16, 158.21, 160.62; IR (KBr cm$^{-1}$): 2975, 2861, 2365, 1642, 1589, 1502, 1227, 1185, 1155, 1111, 1063, 844, 758; EI-MS (70 eV) m/z: 299 ([M+2]$^+$, 0.06%), 297 (M$^+$, 0.3%), 269 (17%), 268 (100%), 255 (17%), 254 (30%), 253 (71%), 252 (16%), 251 (32%), 240 (20%); Anal. calcd for $C_{18}H_{16}FNO_2$: N, 4.71; C, 72.71; H, 5.42. found: N, 4.70; C, 72.77; H, 5.45.

3-Ethoxymethyl-2-(4-chlorophenyl)imino-2H-chromene ($E_4$): (1.00 g, 64%); m.p.: 84~86° C., $R_f$=0.564 (ethyl acetate: n-hexane=1:7); $^1$H-NMR (CDCl$_3$, 400 MHz) δ/ppm: 1.35 (t, J=6.8 Hz, 3H, CH$_2$OCH$_2$CH$_3$), 3.71 (q, J=6.8 Hz, 2H, CH$_2$OCH$_2$CH$_3$), 4.49 (d, J=1.6 Hz, 2H, CH$_2$OCH$_2$CH$_3$), 7.03 (d, J=8.4 Hz, 1H, ArH), 7.12-7.16 (m, 2H, RC=NArH), 7.20 (dd, J=6.8, 1.6 Hz, 1H, ArH), 7.26-7.33 (m, 2H, RC=NArH), 7.35 (dd, J=7.6, 1.2 Hz, 1H, ArH), 7.38 (d, J=8.0 Hz, 1H, ArH), 7.42 (t, J=1.6 Hz, 1H, ArCH=C); $^{13}$C-NMR (CDCl$_3$, 100 MHz) δ/ppm: 15.23, 66.75, 67.42, 115.30, 119.83, 123.79, 124.35, 127.30, 128.60, 128.78, 129.10, 129.77, 130.10, 144.59, 152.11, 162.89; IR (KBr cm$^{-1}$): 2971, 2859, 2361, 1641, 1593, 1483, 1448, 1224, 1182, 1117, 1057, 837, 760; EI-MS (70 eV) m/z: 315 ([M+2]$^+$, 0.2%), 313 (M$^+$, 0.9%), 286 (34%), 285 (23%), 284 (100%), 271 (31%), 270 (29%), 269 (94%), 268 (50%), 256 (20%), 207 (22%); Anal. calcd for C$_{18}$H$_{16}$ClNO$_2$: N, 4.46; C, 68.90; H, 5.14. found: N, 4.31; C, 68.91; H, 5.30.

3-Ethoxymethyl-2-(4-bromophenyl)imino-2H-chromene (E$_5$): (1.16 g, 65%); m.p.: 73~74° C.; Rf=0.590 (ethyl acetate: n-hexane=1:7); $^1$H-NMR (CDCl$_3$, 400 MHz) δ/ppm: 1.34 (t, J=7.2 Hz, 3H, CH$_2$OCH$_2$CH$_3$), 3.71 (q, J=7.2 Hz, 2H, CH$_2$OCH$_2$CH$_3$), 4.48 (d, J=2.0 Hz, 2H, CH$_2$OCH$_2$CH$_3$), 7.04 (d, J=8.4 Hz, 1H, ArH), 7.08 (dt, J=8.8, 2.8 Hz, 2H, RC=NArH), 7.15 (td, J=7.6, 1.2 Hz, 1H, ArH), 7.31 (td, J=8.0, 1.6 Hz, 1H, ArH), 7.36 (dd, J=7.6, 1.6 Hz, 1H, ArH), 7.43 (t, J=2.0 Hz, 1H, ArCH=C), 7.45 (td, J=8.8, 2.4 Hz, 1H, RC=NArH); $^{13}$C-NMR (CDCl$_3$, 100 MHz) δ/ppm: 15.25, 66.79, 67.43, 115.36, 116.60, 119.86, 123.86, 124.76, 127.28, 129.10, 129.85, 130.25, 131.59, 145.11, 148.50, 152.14; IR (KBr cm$^{-1}$): 2973, 2878, 2369, 1637, 1597, 1477, 1218, 1177, 1108, 1061, 1005, 835, 758; EI-MS (70 eV) 359 ([M+2]$^+$, 0.35%), 357 (M$^+$, 0.26%), 330 (73%), 328 (68%), 315 (79%), 314 (63%), 313 (62), 233 (81%), 231 (100%), 220 (66%); Anal. calcd for C$_{18}$H$_{16}$BrNO$_2$: N, 3.91; C, 60.35; H, 4.50. found: N, 3.81; C, 60.37; H, 4.51.

3-Ethoxymethyl-2-(4-ethylphenyl)imino-2H-chromene (E$_6$): (0.98 g, 67%); m.p.: 104~105° C.; Rf=0.564 (ethyl acetate:n-hexane=1:7) $^1$H-NMR (CDCl$_3$, 400 MHz) δ/ppm: 1.37 (t, J=7.2 Hz, 3H, CH$_2$OCH$_2$CH$_3$), 2.39 (s, 3H, RC=NArCH$_3$) 3.74 (q, J=6.8 Hz, 2H, CH$_2$OCH$_2$CH$_3$), 53 (d, J=1.6 Hz, 2H, CH$_2$OCH$_2$CH$_3$), 7.06 (d, J=8.0 Hz, 1H, ArH), 7.13 (td, J=7.6, 1.2 Hz, 1H, ArH) 7.16-7.21 (m, 4H, RC=NArH), 7.29 (td, J=8.0, 1.6 Hz, 1H, ArH), 7.32 dd, J=7.6, 1.6 Hz, 1H, ArH), 7.39 (t, J=1.6 Hz 1H, ArCH=C); $^{13}$C-NMR (CDCl$_3$, 100 MHz) δ/ppm: 15.58, 21.30, 67.04, 67.88, 115.64, 120.28, 123.31, 123.85, 127.42, 129.50, 129.66, 129.79, 129.84, 133.55, 143.56, 147.96, 152.63; IR (KBr cm$^{-1}$): 2971, 2870, 2361, 1651, 1589, 1477, 1415, 1382, 1228, 1178, 1122, 1061, 902, 809, 766, 736, 691; EI-MS (70 eV) m/z: 293 (M$^+$, 0.6%), 265 (19%), 264 (100%), 245 (87%), 249 (21%), 248 (49%), 246 (16%), 236 (10%); Anal. calcd for C$_{18}$H$_{16}$CH$_3$NO$_2$: N, 4.77; C, 77.79; H, 6.53. found: N, 4.67; C, 77.80; H, 6.51.

3-Ethoxymethyl-2-(4-methoxyphenyl)imino-2H-chromene (E$_7$): (1.00 g, 65%); m.p.: 78~79° C., Rf=0.385 (ethyl acetate:n-hexane=1:7); $^1$H-NMR (CDCl$_3$, 400 MHz) δ/ppm: 1.35 (t, J=7.2 Hz, CH$_2$OCH$_2$CH$_3$), 3.72 (q, J=6.8 Hz, 2H, CH$_2$OCH$_2$CH$_3$), 3.83 (s, 3H, RC=NArOCH$_3$), 4.50 (d, J=1.6 Hz, 2H, CH$_2$OCH$_2$CH$_3$), 6.91 (dt, J=9.2, 3.2 Hz, 2H, RC=NArH), 7.07 (d, J=8.0 Hz, 1H, ArH), 7.11 (td, J=7.6, 1.2 Hz, 1H, ArH), 7.28 (dt, J=9.2, 3.2 Hz, 2H, RC=NArH), 7.31-7.34 (m, 2H, ArH), 7.35 (t, J=1.6 Hz, 1H, ArCH=C); $^{13}$C-NMR (CDCl$_3$, 100 MHz) δ/ppm: 15.56, 55.64, 67.01, 67.89, 114.08, 115.57, 120.33, 123.84, 127.96, 127.40, 129.34, 129.79, 129.90, 139.12, 147.57, 152.61, 156.52; IR (KBr cm$^{-1}$): 2969, 2866, 2363, 1648, 1599, 1507, 1446, 1244, 1178, 1113, 1061, 1032, 832, 745; EI-MS (70 eV) m/z: 309 (M$^+$, 5%), 281(150), 280 (75%), 266 (25%), 265 (100%), 264 (15%), 262 (16%), 250 (22%); Anal. calcd for C$_{19}$H$_{19}$NO$_3$: N, 4.53; C, 73.77; H, 6.19. found: N, 4.44; C, 73.78; H, 6.23.

3-Ethoxymethyl-2-(3-methoxyphenyl)imino-2H-chromene (E$_8$): (0.97 g, 63%); Rf=0.410 (ethyl acetate:n-hexane=1:7); $^1$H-NMR (CDCl$_3$, 400 MHz) δ/ppm: 1.34 (t, J=6.8 Hz, 3H, CH$_2$OCH$_2$CH$_3$), 3.71 (q, J=6.8 Hz, 2H, CH$_2$OCH$_2$CH$_3$), 3.82 (s, 3H, RC=NArOCH$_3$), 4.50 (d, J=1.6 Hz, 2H, CH$_2$OCH$_2$CH$_3$), 6.68 (dt, J=8.4, 0.8 Hz, 1H, RC=NArH), 6.75 (t, J=2.0 Hz, 1H, RC=NArH), 6.79 (dt, J=8.0, 0.8 Hz, 1H, RC=NArH), 7.04 (d, J=8.4 Hz, 1H, ArH), 7.12 (td, J=7.6, 1.2 Hz, 1H, ArH), 7.25 (t, J=8.0 Hz, 1H, RC=NArH), 7.29 (td, J=8.0, 1.6 Hz, 1H, ArH), 7.34 (dd, J=7.6, 1.6 Hz, 1H, ArH), 7.40 (t, J=1.6 Hz, 1H, ArCH=C); $^{13}$C-NMR (CDCl$_3$, 100 MHz) δ/ppm: 15.24, 55.18, 66.76, 67.51, 108.31, 109.71, 115.33, 115.43, 119.90, 123.66, 127.18, 129.25, 129.67, 129.85, 147.36, 152.29, 159.99; EI-MS (70 eV) m/z: 309 (M$^+$, 0.5%), 281 (16%), 280 (83%), 266 (31%), 265 (100%), 264 (41%), 263 (22%), 262 (18%); HRMS (ESI, m/z): Calcd. for C$_{19}$H$_{19}$NO$_3$: 309.3591; found: 309.3590.

3-isopropoxymethyl-2-phenylimino-2H-chromene (E$_9$): (1.2.0 q, 82%); m.p.: 107~108° C., Rf=0.605 (ethyl acetate: n-hexane=1:7); $^1$H-NMR (CDCl$_3$, 400 MHz) δ/ppm: 1.30 (d, J=6.0 Hz, 6H, CH$_2$OCH(CH$_3$)$_2$), 3.77-3.84 (m, 1H, CH$_2$OCH(CH$_3$)$_2$), 4.50 (d, J=2.0 Hz, 2H, CH$_2$OCH(CH$_3$)$_2$), 7.01 (d, J=8.0 Hz, 1H, ArH), 7.08-7.13 (m, 2H, RC=NArH), 7.19 (dt, J=6.4, 0.8 Hz, 2H, RC=NArH), 7.27 (td, J=7.6, 1.6 Hz, 1H, ArH), 7.32-7.37 (m, 3H, ArH, RC=NArH), 7.41 (t, J=1.6, 1H, ArCH=C); $^{13}$C-NMR (CDCl$_3$, 100 MHz) δ/ppm: 22.24, 65.25, 72.25, 115.37, 120.00, 122.87, 123.59, 123.67, 127.15, 128.60, 129.54, 12974, 129.83, 146.12, 148.03, 152.25; IR (KBr cm$^{-1}$): 2964, 2873, 2364, 1647, 1590, 1484, 1451, 1370, 1216, 1179, 1124, 1039, 763, 691; EI-MS (70 eV) m/z: 293 (M$^+$, 0.7%), 251 (19%), 250 (100%), 236 (16%), 235 (85%), 234 (64%), 233 (20%), 232 (23%), 222 (23%); Anal. calcd for C$_{19}$H$_{19}$NO$_2$: N, 4.77; C, 77.79; H, 6.53. found: N, 4.68; C, 77.87; H, 6.57.

3-Butoxymethyl-2-phenylimino-2H-chromene (E$_{10}$): (1.32 g, 86%); m.p.: 86~88° C.; Rf=0.651 (ethyl acetate:n-hexane=1:7); $^1$H-NMR (CDCl$_3$, 400 MHz) δ/ppm: 1.00 (t, J=7.2 Hz, 3H, CH$_2$OCH$_2$CH$_2$CH$_2$CH$_3$), 1.44-1.54 (m, 2H, CH$_2$OCH$_2$CH$_2$CH$_2$CH$_3$), 1.68-1.75 (m, 2H, CH$_2$OCH$_2$CH$_2$CH$_2$CH$_3$), 3.58 (t, J=6.4 Hz, 2H, CH$_2$OCH$_2$CH$_2$CH$_2$CH$_3$), 4.51 (d, J=2.0 Hz, 2H, CH$_2$O(CH$_2$)$_3$CH$_3$), 7.04 (d, J=8.4 Hz, 1H, ArH), 7.10-7.15 (m, 2H, RC=NArH), 7.21 (dt, J=6.8, 1.6 Hz, 2H, RC=NArH), 7.29 (td, J=8.0, 1.6 Hz, 1H, ArH), 7.34-7.39 (m, 3H, ArH, RC=NArH), 7.40 (t, J=1.6, 1H, ArCH=C); $^{13}$C-NMR (CDCl$_3$, 100 MHz) δ/ppm: 13.95, 19.40, 31.84, 67.71, 71.23, 115.39, 119.95, 122.88, 123.60, 123.69, 127.16, 128.59, 129.45, 129.60, 129.68, 146.09, 147.92, 152.29; IR (KBr cm$^{-1}$): 2955, 2864, 2367, 1646, 1590, 1482, 1450, 1381, 1216, 1180, 1113, 1071, 759, 689; EI-MS (70 eV) m/z: 307 (M$^+$, 0.5%), 251 (18%), 250 (100%), 237 (16%), 235 (84%), 234 (72%), 233 (16%), 232 (21%), 222 (16%); Anal. calcd for C$_{20}$H$_{21}$NO$_2$: N, 4.56; C, 78.15; H, 6.89. found: N, 4.46; C, 78.14; H, 6.87.

6-Chloro-3-ethoxymethyl-2-phenylimino-2H-chromene (E$_{11}$): (1.06 g, 68%); m.p.: 58~59° C., Rf=0.465 (ethyl acetate:n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=6.8 Hz, 2H, CH$_2$OCH$_2$CH$_3$), 4.49 (d, J=1.6 Hz, 2H, CH$_2$OCH$_2$CH$_3$), 6.95 (d, J=8.8 Hz, 1H, ArH), 7.11 (tt, J=7.6, 0.8 Hz, 1H, RC=NArH), 7.13 (dt, J=7.6, 1.2 Hz, 2H, RC=NArH), 7.22 (dd, J=8.8, 2.8 Hz, 1H, ArH), 7.31-7.38 (m, 4H, ArH, ArCH=C, RC=NArH); $^{13}$C-NMR (CDCl$_3$, 100 MHz) δ/ppm: 15.24, 66.83, 67.43, 116.14, 121.19, 122.81, 123.97, 126.48, 128.43, 128.64, 129.39, 130.80, 145.68, 147.17, 150.70; IR (KBr cm$^{-1}$): 2972, 2871, 2358, 1651, 1590, 1479, 1418, 1382, 1226, 1178, 1121, 1060, 902, 810, 766, 736, 690; ET-MS (70 eV) m/z: 315 ([M+2]$^+$, 0.5%), 313 (M$^+$, 0.4%), 286 (34%), 285 (23%), 284 (100%) 271 (79%), 270 (37%), 269 (53%), 268 (39%); Anal. calcd for $C_{18}H_{16}ClNO_2$: N, 4.46; C, 68.90; H, 5.14. found: N, 4.37; C, 68.89; H, 5.13.

6-Chloro-3-ethoxymethyl-2-(4-fluorophenyl)imino-2H-chromene ($E_{12}$): (1.06 g, 64%); m.p.: 36-137° C., $R_f$=0.419 (ethyl acetate:n-hexane=1:7); $^1$H-NMR (CDCl$_3$, 400 MHz) δ/ppm: 1.33 (t, J=7.2 Hz, 3H, CH$_2$OCH$_2$CH$_3$), 3.70 (g, J=7.2 Hz, 2H, CH$_2$OCH$_2$CH$_3$), 4.47 (d, J=2.0 Hz, 2H, CH$_2$OCH$_2$CH$_3$), 6.98 (d, J=8.8 Hz, 1H, ArH) 7.01-7.05 (m, 2H, RC=NArH), 7.16-7.19 (m, 2H, RC=NArH), 7.25 (dd, J=8.8, 2.4 Hz, 1H, ArH), 7.32 (t, J=2.0 Hz, 1H, ArCH=C), 7.33 (d, J=2.4 Hz, 1H, ArH); $^{13}$C-NMR (CDCl$_3$, 100 MHz) δ/ppm: 15.23, 66.86, 67.41, 1145.18, 115.40, 116.68, 121.20, 124.40, 124.48, 126.58, 128.56, 129.48, 130.78, 150.63, 158.40, 160.81; IR (KBr cm$^{-1}$): 2970, 2866, 2367, 1653, 1500, 1419, 1182, 1120, 1064, 907, 816; ET-MS (70 eV) m/z: 333 [M+2]$^+$, 0.05%), 331 (M$^+$, 0.5%), 304 (31%), 303 (20%), 302 (91%), 290 (24%), 288 (100%), 286 (45%), 274 (14%); Anal. calcd for $C_{18}H_{15}ClFNO_2$: N, 4.22; C, 65.16; H, 4.56. found: N, 4.15; C, 65.18; H, 4.66.

6-Chloro-3-ethoxymethyl-2-(4-chlorophenyl)imino-2H-chromene ($E_{13}$): (1.15 g, 66%); m.p.: 126~128° C., $R_f$=0.488 (ethyl acetate:n-hexane=1:7); $^1$H-NMR (CDCl$_3$, 400 MHz) δ/ppm: 1.33 (t, J=7.6 Hz, 3H, CH$_2$OCH$_2$CH$_3$), 3.70 (q, J=6.8 Hz, 2H, CH$_2$OCH$_2$CH$_3$), 4.47 (d, J=2.0 Hz, 2H, CH$_2$OCH$_2$CH$_3$), 6.98 (d, J=8.8 Hz, 1H, ArH), 7.11 (dt, J=9.6, 2.8 Hz, 2H, RC=NArH), 7.24-7.27 (m, 2H, RC=NArH), 7.30 (dd, J=8.8, 2.4 Hz, 1H, ArH), 7.32 (d, J=2.4 Hz, 1H, ArH), 7.33 (t, J=1.6 Hz, 1H, ArCH=C); $^{13}$C-NMR (CDCl$_3$, 100 MHz) δ/ppm: 15.22, 66.87, 67.36, 116.71, 117.94, 121.15, 124.29, 126.61, 128.71, 128.89, 129.58, 130.64, 130.92, 136.68, 150.60, 159.83; IR (KBr cm$^{-1}$): 2972, 2866, 2366, 1647, 1480, 1418, 1258, 1181, 1121, 1063, 1004, 892, 812; EI-MS (70 eV) m/z: 349 ([M+2]$^+$, 0.14%), 347 (M$^+$, 0.4%) 320 (70%), 319 (100%), 306 (59%), 305 (53%), 304 (91%), 302 (47%), 207 (37%); Anal. calcd for $C_{18}H_{15}Cl_2NO_2$: N, 4.02; C, 62.08; H, 4.34. found: N, 4.01; C, 62.11; H, 38.

6-Chloro-3-ethoxymethyl-2-(4-bromophenyl)imino-2H-chromene ($E_{14}$): (1.23 g, 63%); m.p.: 119~121° C.; $R_f$=0.465 (ethyl acetate:n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=6.8 Hz, 2H, CH$_2$OCH$_2$CH$_3$), 4.46 (d, J=2.0 Hz, 2H, CH$_2$OCH$_2$CH$_3$), 6.97 (d, J=8.8 Hz, 1H, ArH), 7.05 (dt, J=8.8, 2.0 Hz, 2H, RC=NArH), 7.25 (dd, J=8.4, 2.4 Hz, 1H, ArH), 7.33-7.34 (m, 2H, ArH, ArCH=C), 7.45 (dt, J=8.4, 2.0 Hz, 2H, RC=NArH); $^{13}$C-NMR (CDCl$_3$, 100 MHz) δ/ppm: 15.23, 66.87, 67.34, 116.70, 116.89, 121.14, 124.68, 126.60, 128.92, 129.58, 130.63, 131.66, 144.78, 147.69, 150.58; IR (KBr cm$^{-1}$): 2970, 2866, 2367, 1647, 1590, 1500, 1470, 1418, 1381, 1230, 1179, 1118, 1060, 900, 80; EI-MS (70 eV) m/z: 393 ([M+2]$^+$, 0.14%), 391 (M$^+$, 0.19%), 366 (26%), 364 (100%), 362 (75%), 350 (32%), 349 (94%), 348 (69%), 347 (80%); Anal. calcd for $C_{18}H_{15}BrClNO_2$: N, 3.57; C, 55.06; H, 3.85. found: N, 3.49; C, 55.08; H, 3.89.

6-Chloro-3-ethoxymethyl-2-(4-methylphenyl)imino-2H-chromene ($E_{15}$): (1.10 g, 67%); m.p.: 76~77° C., $R_f$=465 (ethyl acetate:n-hexane=1:7); $^1$H-NMR (CDCl$_3$, 400 MHz) δ/ppm: 1.33 (t, J=7.2 Hz, 3H, CH$_2$OCH$_2$CH$_3$), 2.35 (s, 3H, RC=NArCH$_3$), 3.70 (q, J=7.2 Hz, 2H, CH$_2$OCH$_2$CH$_3$), 4.48 (d, J=1.6 Hz, 2H, CH$_2$OCH$_2$CH$_3$), 6.97 (d, J=8.8 Hz, 1H, ArH), 7.10-7.16 (m, 4H, RC=NArH), 7.22 (dd, J=8.8, 2.4 Hz 1H, ArH), 7.29 (t, J=2.0 Hz, 1H, ArCH=C), 7.30 (d, J=2.0 Hz, 1H, ArH); $^{13}$C-NMR (CDCl$_3$, 100 MHz) δ/ppm: 15.24, 21.00, 66.82, 67.49, 116.70, 121.28, 122.94, 126.46, 128.13, 128.59, 129.24, 129.30, 130.98, 133.61, 142.87, 146.94, 150.78; IR (KBr cm$^{-1}$): 2963, 2858, 2367, 1644, 1478, 1414, 1381, 1265, 1220, 1181, 1122, 1064, 900, 810; EI-MS (70 eV) m/z: 329 ([M+2]$^+$, 0.48%), 327 (M$^+$, 0.72%), 300 (33%), 299 (22%) 298 (100%), 286 (30%), 285 (67%), 284 (98%), 282 (55%); Anal. calcd for $C_{19}H_{18}ClNO_2$: N, 4.27; C, 69.62; H, 5.53. found: N, 4.25; C, 69.58; H, 5.54.

6-Chloro-3-ethoxymethyl-2-(4-methoxyphenyl)imino-2H-chromene ($E_{16}$): (1.10 q, 64%); m.p.: 136~138° C., $R_f$=0.302 (ethyl acetate:n hexane=1:7); $^1$H-NMR (CDCl$_3$, 400 MHz) δ/ppm: 1.33 (t, J=7.2 Hz, 3H, CH$_2$OCH$_2$CH$_3$), 3.70 (q, J=6.8 Hz, 2H, CH$_2$OCH$_2$CH$_3$), 3.83 (s, 3H, RC=NArOCH$_3$), 4.48 (d, J=1.6 Hz, 2H, CH$_2$OCH$_2$CH$_3$), 6.90 (dt, 8.8, 2.4 Hz, 2H, RC=NArH), 7.01 (d, J=8.4 Hz, ArH), 7.22-7.26 (m, 3H, ArH, RC=NArH), 7.27 (t, J=2.0 Hz, 1H, ArCH=C), 7.31 (d, J=2.4 Hz, 1H, ArH); $^{13}$C-NMR (CDCl$_3$, 100 MHz) δ/ppm: 15.25, 55.42, 66.82, 67.53, 113.87, 116.65, 121.38, 124.71, 126.47, 127.82, 128.60, 129.27, 131.13, 138.45, 146.55, 150.80, 156.48; IR (KBr cm$^{-1}$): 2977, 2861, 2365, 1643, 1597, 1507, 1418, 1242, 1179, 1133, 1062, 1023, 816; EI-MS (70 eV) m/z: 345 ([M+2]$^+$, 3%), 343 (M$^+$, 9%), 316 (34%), 315 (23%), 314 (96%), 302 (35%), 300 (49%), 299 (100%), 298 (34%), 284 (23%); Anal. calcd for $C_{19}H_{18}ClNO_3$: N, 4.07; C, 66.38; H, 5.28. found: N, 4.02; C, 66.33; H, 5.27.

6-Chloro-3-ethoxymethyl-2-(3-methoxyphenyl)imino-2H-chromene ($E_{17}$): (1.13 g, 66%); m.p.: 96.5~97.5° C., $R_f$=0.326 (ethyl acetate:n-hexane=1:1); $^1$H-NMR (CDCl$_3$, 400 MHz) δ/ppm: 1.34 (t, J=7.2 Hz, 3H, CH$_2$OCH$_2$CH$_3$), 3.71 (q, J=7.2 Hz, 2H, CH$_2$OCH$_2$CH$_3$), 3.82 (s, 3H, RC=NArOCH$_3$), 4.49 (d, J=1.6 Hz, 2H, CH$_2$OCH$_2$CH$_3$), 6.69 (dt, J=8.4, 0.8 Hz, 1H, RC=NArH), 6.74 (t, J=2.0 Hz, 1H, RC=NArH), 6.78 (dt, J=8.0, 0.8 Hz, 1H, RC=NArH), 6.98 (d, J=8.4 Hz, 1H, ArH), 7.21 (dd, J=8.0, 2.4 Hz, 1H, ArH) 7.25 (t, J=8.0 Hz, 1H, RC=NArH), 7.31 (m, 2H, ArCH=C, ArH); $^{13}$C-NMR (CDCl$_3$, 100 MHz) δ/ppm: 15.20, 55.16, 66.79, 67.38, 108.33, 109.80, 115.20, 116.73, 121.12, 126.46, 128.51, 129.27, 129.36, 130.72, 146.94, 150.67, 159.98; IR (KBr cm$^{-1}$): 2970, 2862, 2364, 1650, 1584, 1480, 1268, 1231, 1180, 1123, 1065, 908, 853, 807, 781; EI-MS (70 eV) m/z: 345 ([M+2]$^+$, 0.7%), 343 (M$^+$, 0.24%), 316 (18%), 314 (55%), 302 (13%), 301.5 (16%), 300 (100%), 298 (33%), 297 (15%), 296 (15%); Anal. calcd for $C_{19}H_{18}ClNO_3$: N, 4.07; C, 66.38; H, 5.28. found: N, 4.00; C, 66.40; H, 5.26.

6-Bromo-3-ethoxymethyl-2-phenylimino-2H-chromene ($E_{18}$): (1.16 g, 64%) m.p.: 78~80° C., $R_f$=0.452 (ethyl acetate: n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=7.2, Hz, 2H, CH$_2$OCH$_2$CH$_3$), 4.49 (d, J=2.0 Hz, 2H, CH$_2$OCH$_2$CH$_3$), 6.90 (d, J=8.8 Hz, 1H, ArH), 7.08 (tt, J=8.8, 0.8 Hz, 1H, RC=NArH), 7.17 (dt, J=8.4, 2.4 Hz, 2H, RC=NArH), 7.30 (t, J=2.0, 1H, ArCH=C) 7.32-7.37 (m, 3H, ArH, RC=NArH), 7.46 (d, J=2.4 Hz, 1H, ArH); $^{13}$C-NMR (CDCl$_3$, 100 MHz) δ/ppm: 15.23, 66.82, 67.42, 115.99, 117.09, 121.69, 122.81, 123.98, 128.33, 128.64, 129.47, 130.79, 132.24, 145.62, 147.09, 151.19; IR (KBr cm$^{-1}$): 2971, 2870, 2361, 1651, 1589, 1415, 1382, 1228, 1178, 1122, 1061, 902, 809, 766, 736, 691; EI-MS (70 eV) m/z: 359 ([M+2]$^+$, 1.4%), 357 (M$^+$, 1.4%), 330 (98%), 329 (100%), 316 (79%), 315 (68%), 314 (90%), 312 (55%); Anal. calcd for $C_{18}H_{16}BrNO_2$: N, 3.91; C, 60.35; H, 4.50. found: N, 3.68; C, 60.19; H, 4.78.

6-Bromo-3-ethoxymethyl-2-(4-fluorophenyl)imino-2H-chromene ($E_{19}$): (1.22 g, 65%); m.p.: 153~154° C.; $R_f$=0.429 (ethyl acetate:n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=7.2, Hz, 2H, CH$_2$OCH$_2$CH$_3$), 4.47 (d, J=2.0 Hz, 2H, CH$_2$OCH$_2$CH$_3$), 6.92 (d, J=8.8 Hz, 1H, ArH), 7.01-7.06 (m, 2H, RC=NArH), 7.15-7.19 (m, 2H, RC=NArH), 7.31 (t, J=1.6, 1H, ArCH=C), 7.39 (dd, J=8.8, 2.4 Hz, 1H, ArH), 7.47 (d, J=2.4 Hz, 1H, ArH); $^{13}$C-NMR (CDCl$_3$, 100 MHz) δ/ppm: 15.23, 66.84, 67.40, 115.17, 115.40, 116.14, 117.02, 121.70, 124.40, 128.39, 129.55, 130.77, 132.31, 151.11, 158.39, 160.80; IR (KBr cm$^{-1}$): 2972, 2866, 2363, 1650, 1591, 1499, 1414, 1383, 1183, 1122, 1062, 908, 818, 781; EI-MS (70 eV) m/z: 377 ([M+2]$^+$, 0.14%), 375 (M$^+$, 0.03%), 348 (63%), 347 (60%), 334 (86%), 332 (100%), 238 (64%), 237 (49%); Anal. calcd for C$_{18}$H$_{15}$BrFNO$_2$: N, 3.72; C, 57.46; H, 4.02. found: N, 3.65; C, 57.56; H, 4.05.

6-Bromo-3-ethoxymethyl-2-(4-chlorophenyl)imino-2H-chromene (E$_{20}$): (1.27 g, 62%); m.p.: 144~145° C., R$_f$=0.476 (ethyl acetate:n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=6.8 Hz, 2H, CH$_2$OCH$_2$CH$_3$), 4.47 (d, J=2.0 Hz, 2H, CH$_2$OCH$_2$CH$_3$), 6.92 (d, J=8.8 Hz, 1H, ArH) 7.11 (dt, J=8.8, 3.2 Hz, 2H, RC=NArH), 7.30 (dt, J=8.8, 2.8 Hz, 2H, RC=NArH), 7.33 (t, J=2.0, 1H, ArCH=C), 7.39 (dt, J=8.8, 2.4 Hz, 1H, ArH), 7.48 (d, J=2.0 Hz, 1H, ArH); $^{13}$C-NMR (CDCl$_3$, 100 MHz) δ/ppm: 15.22, 66.86, 67.34, 116.23, 117.05, 121.64, 124.29, 128.71, 128.74, 129.13, 129.58, 130.64, 132.42, 144.22, 147.61, 151.07; IR (KBr cm$^{-1}$): 2971, 2863, 2361, 1646, 1599, 1477, 1382, 1225, 1180, 1122, 1063, 904, 811; EI-MS (70 eV) m/z: 393 ([M+2]$^+$, 0.02%), 391 (M$^+$, 0.02%), 364 (100%), 363 (81%), 351 (35%), 350 (90%), 349 (60%), 348 (73%), 346 (33%); Anal. calcd for C$_{18}$H$_{15}$BrClNO$_2$: N, 3.57; C, 55.06; H, 3.85. found: N, 3.51; C, 55.00; H, 3.95.

6-Bromo-3-ethoxymethyl-2-(4-bromophenyl)imino-2H-chromene (E$_{21}$): (1.35 g, 62%); m.p.: 129~431° C., R$_f$=0.500 (ethyl acetate:n-hexane=1:7); $^1$H-NMR (CDCl$_3$, 400 MHz) δ/ppm: 1.33 (t, J=7.2 Hz, 3H, CH$_2$OCH$_2$CH$_3$), 3.70 (q, J=6.8 Hz, 2H, CH$_2$OCH$_2$CH$_3$), 4.47 (d, J=1.6 Hz, 2H, CH$_2$OCH$_2$CH$_3$), 6.92 (dd, J=8.8, 2.0 Hz, 1H, ArH), 7.05 (dt, J=8.4, 3.2 Hz, 2H, RC=NArH), 7.34 (t, J=1.6 Hz, 1H, ArCH=C), 7.40 (dd, J=8.8, 2.4 Hz, 1H, ArH), 7.44-7.51 (m, 2H, RC=NArH), 7.55 (dd, J=9.2, 2.0 Hz, 1H, ArH); $^{13}$C-NMR (CDCl$_3$, 100 MHz) δ/ppm: 15.22, 66.87, 67.33, 116.27, 117.07, 121.63, 124.69, 128.86, 129.60, 130.59, 131.70, 132.47, 132.60, 144.68, 147.67, 151.05; IR (KBr cm$^{-1}$): 2971, 2866, 2362, 1644, 1476, 1382, 1180, 1122, 1064, 903, 827; EI-MS (70 eV) m/z: 438 ([M+2]$^+$, 0.31%), 434 (M$^+$, 0.01%), 408 (61%), 396 (47%), 394 (96%), 392 (66%), 312 (100%), 311 (51%), 310 (58%); Anal. calcd for C$_{18}$H$_{15}$Br$_2$NO$_2$: N, 3.46; C, 49.46; H, 3.46. found: N, 3.15; C, 48.40; H, 3.40.

6-Bromo-3-ethoxymethyl-2-(4-methylphenyl)imino-2H-chromene (E$_{22}$): (1.22 g, 66%); m.p.: 116~117° C., R$_f$=0.500 (ethyl acetate:n-hexane=1:7); $^1$H-NMR (CDCl$_3$, 400 MHz) δ/ppm: 1.32 (t, J=7.2 Hz, 3H, CH$_2$OCH$_2$CH$_3$), 2.35 (s, 3H, RC=NArCH$_3$), 3.69 (q, J=6.8 Hz, 2H, CH$_2$OCH$_2$CH$_3$), 4.48 (d, J=1.6 Hz, 2H, CH$_2$OCH$_2$CH$_3$), 6.91 (d, J=8.8 Hz, 1H, ArH), 7.10-716 (m, 4H, RC=NArH) 7.27 (t, J=1.6 Hz, 1H, ArCH=C), 7.36 (dd, J=8.8, 2.4 Hz, 1H, ArH), 7.44 (d, J=2.0 Hz, 1H, ArH); $^{13}$C-NMR (CDCl$_3$, 100 MHz) δ/ppm: 15.23, 20.99, 66.79, 67.46, 76.68, 117.04, 121.77, 122.94, 127.96, 129.23, 129.42, 130.96, 132.14, 133.60, 142.83, 146.79, 151.24; IR (KBr cm$^{-1}$) 2971, 2874, 2362, 1652, 1592, 1507, 1222, 1182, 1120, 1063, 908, 814; EI-MS (70 eV) m/z: 373 ([M+2]$^+$, 1.3%), 371 (M$^+$, 1.3%), 344 (87%), 343 (87%), 330 (87%), 329 (45%), 328 (100%), 32% (36%), 326 (29%); Anal. calcd for C$_{19}$H$_{18}$BrNO$_7$: N, 3.76; C, 61.30; H, 4.87. found: N, 3.74; C, 61.18; H, 4.83.

6-Bromo-3-ethoxymethyl-2-(4-methoxyphenyl)imino-2H-chromene (E$_{23}$): (1.30 g, 67%); m.p.: 134~135° C., R$_f$=0.309 (ethyl acetate:n-hexane=1:7); $^1$H-NMR (CDCl$_3$, 400 MHz) δ/ppm: 1.32 (t, J=6.8 Hz, CH$_2$OCH$_2$CH$_3$), 3.69 (q, J=7.2 Hz, 2H, CH$_2$OCH$_2$CH$_3$), 3.82 (s, 3H, RC=NArOCH$_3$), 4.47 (d, J=2.0 Hz, 2H, CH$_2$OCH$_2$CH$_3$), 6.89 (dt, J=7.2, 2.0 Hz, 2H, RC=NArH), 6.94 (d, J=8.4 Hz, 1H, ArH), 7.22-7.26 (m, 3H, RC=NArH, ArCH=C), 7.37 (dd, J=8.4, 2.4 Hz, 1H ArH), 7.45 (d, J=2.0 Hz, 1H, ArH); $^{13}$C-NMR (CDCl$_3$, 100 MHz) δ/ppm: 15.24, 55.40, 66.79, 67.50 113.84, 115.91, 116.99, 121.87, 124.72, 127.65, 129.43, 131.12, 132.10, 138.40, 146.39, 151.26, 156.46; IR (KBr cm$^{-1}$): 2976, 2869, 2365, 1642, 1593, 1505, 1413, 1382, 1241, 1178, 1126, 1060, 1025, 815; EI-MS (70 eV) m/z: 389 ([M+2]$^+$, 0.5%), 387 (M$^+$, 0.8%), 360 (33%), 358 (36%), 345 (60%), 344 (37%), 343 (100%), 331 (24%), 328 (27%); Anal. calcd for C$_{19}$H$_{18}$BrNO$_3$: N, 3.61; C, 58.78; H, 4.67. found: N, 3.61; C, 58.70; H, 4.65.

6-Bromo-3-ethoxymethyl-2-(3-methoxyphenyl)imino-2H-chromene (E$_{24}$): (1.23 g, 65%); m.p.: 93~94° C., R$_f$=0.357 (ethyl acetate:n-hexane=1:7); $^1$H-NMR (CDCl$_3$, 400 MHz) δ/ppm: 1.33 (t, J=6.8 Hz, 3H, CH$_2$OCH$_2$CH$_3$), 3.70 (q, J=7.2 Hz, 2H, CH$_2$OCH$_2$CH$_3$), 3.81 (s, 3H, RC=NArOCH$_3$), 4.84 (d, J=1.6 Hz, 2H, CH$_2$OCH$_2$CH$_3$), 6.68 (dt, J=8.4, 0.8 Hz, 1H, RC=NArH), 6.72 (t, J=2.0 Hz, 1H, RC=NArH), 6.77 (dt, J=8.0, 0.8 Hz, 1H, RC=NArH), 6.92 (d, J=8.8 Hz, 1H, ArH), 7.25 (t, J=8.0 Hz, 1H, RC=NArH), 7.31 (t, J=1.6 Hz, 1H, ArCH=C), 7.37 (dd, J=8.8, 2.4 Hz 1H ArH), 7.47 (d, J=2.4 Hz 1H ArH); $^{13}$C-NMR (CDCl$_3$, 100 MHz) δ/ppm: 15.22, 55.20, 66, 82, 67.39, 108.32, 109.85, 115.19, 116.03, 117.14, 121.66, 128.345, 129.48, 130.72, 132.27, 146.93, 151.19, 160.00; IR (KBr cm$^{-1}$): 2970, 2361, 1648, 1584, 1477, 1268, 1232, 1182, 1121, 1065, 904, 807, 783; EI-MS (70 eV) m/z: 389 ([M+2]$^+$, 0.4%), 387 (M$^+$, 0.6%), 360 (44%), 359 (11%), 358.5 (44%), 346 (62%), 345 (47%), 344 (100%), 342 (25%); Anal. calcd for C$_{19}$H$_{18}$BrNO$_3$: N, 3.61; C, 58.78; H, 4.67. found: N, 3.61; C, 58.80; H, 4.70.

7-Benzyloxy-3-ethoxymethyl-(Z)-2-phenylimino-2H-chromene (E$_{25}$): (1.19 g, 62%); m.p.: 94-95° C., R$_f$=0.40 (ethyl acetate:n-hexane=1:9); IR (KBr cm$^{-1}$): 2973, 2867, 1649, 1612, 1505, 1385, 1262, 1164, 1130, 1065, 695; $^1$H-NMR (400 MHz, CDCl$_3$) δ/ppm: 1.32 (3H, t, J=6.8 Hz, OCH$_2$CH$_3$), 3.70 (2H, q, J=6.8 Hz, OCH$_2$CH$_3$), 4.48 (2H, d, J=1.6 Hz, CH$_2$OCH$_2$CH$_3$), 4.99 (2H, s, OCH$_2$Ph), 6.64 (1H, d, J=2.4 Hz, H-8), 6.76 (1H, dd, J=8.4, 2.4 Hz, H-6), 7.10 (1H, t, J=7.6 Hz, ArH), 7.17 (2H, d, J=7.6 Hz, ArH), 7.22 (1H, d, J=8.4 Hz, H-5), 7.30-7.39 (8H, m, H-4 and ArH); $^{13}$C-NMR (100 MHz, CDCl$_3$) δ/ppm: 15.3, 66.7, 67.5, 70.2, 101.2, 111.6, 113.6, 122.8, 123.5, 126.2, 127.5, 127.9, 128.1, 128.6, 128.6, 129.9, 136.1, 146.3, 148.1, 153.6, 160.3; MS (EI): 385 (M$^+$, 0.2%), 250 (42%), 91 (100%); Anal. calcd for C$_{25}$H$_{23}$NO$_3$ (385.46): C, 77.90; H, 6.01; N, 3.63. found: C, 77.94; H, 6.00; N, 3.60.

7-Methoxy-3-ethoxymethyl-(Z)-2-phenylimino-2H-chromene (E$_{26}$): (0.87 g, 57%); mp 107-108° C., R$_f$=0.40 (ethyl acetate:n-hexane=1:9); IR (KBr cm$^{-1}$): 2973, 2868, 1649, 1610, 1508, 1486, 1445, 1389, 1264, 1159, 1131, 1064, 759; $^1$H-NMR (400 MHz, CDCl$_3$) δ/ppm: 1.33 (3H, t, J=6.8 Hz, OCH$_2$CH$_3$), 3.71 (2H, q, J=6.8, Hz, OCH$_2$CH$_3$), 3.77 (3H, OCH$_3$), 4.48 (2H, d, J=1.6 Hz, CH$_2$OCH$_2$CH$_3$), 6.55 (1H, J=2.4 Hz, H-8), 6.69 (1H, dd, J=8.4, 2.4, H-6), 7.10 (1H, tt, J=7.6, 1.2 Hz, ArH), 7.16-7.19 (2H, m, ArH), 7.23 (1H, d, J=8.4 Hz, H-5), 7.33-7.37 (2H, m, ArH), 7.34 (1H, t, J=1.6 Hz, H-4); $^{13}$C-NMR (100 MHz, CDCl$_3$) δ/ppm: 15.3, 55.6, 66.7, 67.5, 100.1, 111.1, 113.3, 122.8, 123.5, 126.0, 127.9, 128.6, 129.9, 146.3, 148.2, 153.7, 161.2; MS (EI): 309 (M$^+$, 0.5%), 280 (100%) 265 (94%), 264 (72%), 252 (60%); Anal. calcd for C$_{19}$H$_{19}$NO$_3$ (309.36): C, 73.77; H, 6.19; N, 4.53. found: C, 73.87, H, 6.09; N, 11.46.

8-Methoxy-3-ethoxymethyl-(Z)-2-phenylimino-2H-chromene (E$_{27}$): (1.04 g, 67%); m.p.: 88-90° C., R$_f$=0.43 (ethyl acetate:n-hexane=1:9); IR (KBr cm$^{-1}$): 2972, 2866, 1645, 1586, 1482, 1269, 1224, 1183, 1106, 1062, 765; $^1$H-NMR (400 MHz, CDCl$_3$) δ/ppm: 1.34 (3H, t, J=6.8 Hz, OCH$_2$CH$_3$), 3.72 (2H, q, J=6.8 Hz, OCH$_2$CH$_3$), 3.81 (3H, s, OCH$_3$), 4.52 (2H, d, J=1.6 Hz, CH$_2$OCH$_2$CH$_3$), 6.90 and 6.95

(each 1H, dd, J=8.0, 1.6 Hz, H-5 and H-7), 7.05 (1H, t, J=8.0 Hz, H-6), 7.11 (1H, tt, J=7.2, 1.2 Hz, ArH), 7.33-7.37 (2H, m, ArH), 7.37 (1H, t, J=1.6 Hz, H-4), 7.41-7.44 (2H, m, ArH); $^{13}$C-NMR (100 MHz, CDCl$_3$) δ/ppm: 15.3, 56.6, 66.8, 67.6, 113.1, 119.2, 120.7, 123.4, 124.0, 124.1, 125.5, 129.6, 129.7, 142.1, 145.5, 146.9, 147.4; MS (EI): 309 (M$^+$, 0.5%), 280 (100%), 265 (95%), 264 (70%); Anal. calcd. For Cl$_{19}$H$_{19}$NO$_3$ (309.36): C, 73.77; H, 6.19; N, 4.53. found: C, 73.79; H, 6.21; N, 4.50.

Examples 28-36

Preparation of the Coumarin Compounds [(F$_1$)~(F$_9$)]

Each of the coumarin compounds (F$_1$)~(F$_9$) was prepared according to scheme III below by: dissolving 1.0 mmol of a corresponding one of the chromene compounds (E$_1$)(E$_2$)(E$_9$)(E$_{10}$)(E$_{11}$)(E$_{18}$)(E$_{25}$)(E$_{26}$) and (E$_{27}$) into 10 mL of THF to form a coumarin solution, and adding 5 mL, 15 wt% of HCl aqueous solution into the coumarin solution at 0° C. to form a reaction solution, followed by raising the reaction solution from 0° C. to room temperature under a nitrogen gas for 30 mins.

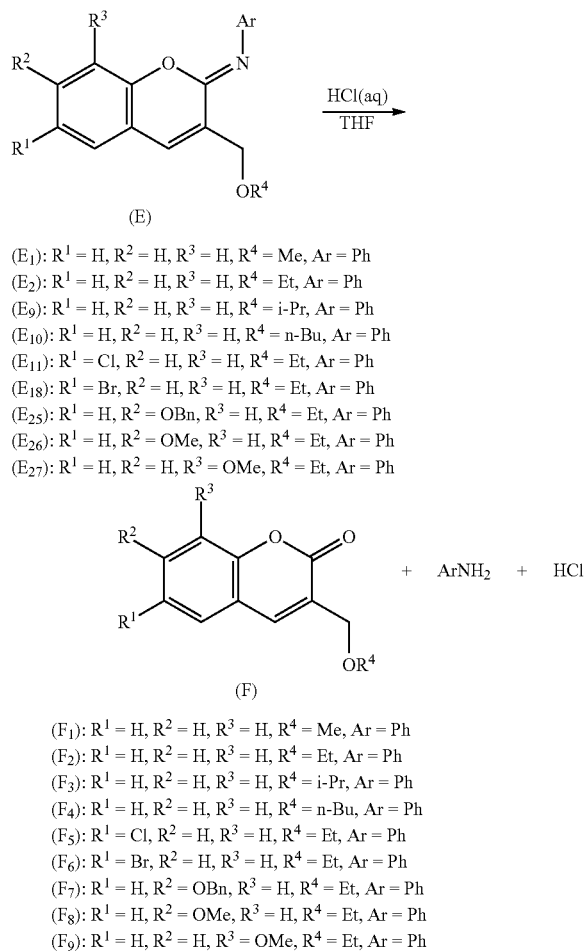

Scheme III (E$_1$): R$^1$ = H, R$^2$ = H, R$^3$ = H, R$^4$ = Me, Ar = Ph
(E$_2$): R$^1$ = H, R$^2$ = H, R$^3$ = H, R$^4$ = Et, Ar = Ph
(E$_9$): R$^1$ = H, R$^2$ = H, R$^3$ = H, R$^4$ = i-Pr, Ar = Ph
(E$_{10}$): R$^1$ = H, R$^2$ = H, R$^3$ = H, R$^4$ = n-Bu, Ar = Ph
(E$_{11}$): R$^1$ = Cl, R$^2$ = H, R$^3$ = H, R$^4$ = Et, Ar = Ph
(E$_{18}$): R$^1$ = Br, R$^2$ = H, R$^3$ = H, R$^4$ = Et, Ar = Ph
(E$_{25}$): R$^1$ = H, R$^2$ = OBn, R$^3$ = H, R$^4$ = Et, Ar = Ph
(E$_{26}$): R$^1$ = H, R$^2$ = OMe, R$^3$ = H, R$^4$ = Et, Ar = Ph
(E$_{27}$): R$^1$ = H, R$^2$ = H, R$^3$ = OMe, R$^4$ = Et, Ar = Ph (F)

(F$_1$): R$^1$ = H, R$^2$ = H, R$^3$ = H, R$^4$ = Me, Ar = Ph
(F$_2$): R$^1$ = H, R$^2$ = H, R$^3$ = H, R$^4$ = Et, Ar = Ph
(F$_3$): R$^1$ = H, R$^2$ = H, R$^3$ = H, R$^4$ = i-Pr, Ar = Ph
(F$_4$): R$^1$ = H, R$^2$ = H, R$^3$ = H, R$^4$ = n-Bu, Ar = Ph
(F$_5$): R$^1$ = Cl, R$^2$ = H, R$^3$ = H, R$^4$ = Et, Ar = Ph
(F$_6$): R$^1$ = Br, R$^2$ = H, R$^3$ = H, R$^4$ = Et, Ar = Ph
(F$_7$): R$^1$ = H, R$^2$ = OBn, R$^3$ = H, R$^4$ = Et, Ar = Ph
(F$_8$): R$^1$ = H, R$^2$ = OMe, R$^3$ = H, R$^4$ = Et, Ar = Ph
(F$_9$): R$^1$ = H, R$^2$ = H, R$^3$ = OMe, R$^4$ = Et, Ar = Ph

The reaction solution was mixed with a saturated NaCl aqueous solution after the reaction was completed. The reaction product in the reaction solution was subsequently extracted using CH$_2$Cl$_2$, and was cleaned with a saturated NaHCO$_3$ aqueous solution, dried, filtered, and concentrated, so as to obtain a colorless crystal of a coumarin compound of formula (F).

Structure Identification of the Coumarin Compounds [(F$_1$)~(F$_9$)]

3-Methoxymethylcoumarin (F$_1$): (0.13 g, 68); m.p.: 72-73° C., R$_f$=0.33 (ethyl acetate:n-hexane=1.5)); IR (KBr cm$^{-1}$): 2957, 2919, 1713, 1603, 1454, 1394, 1168, 1115, 1043, 1010, 925, 780, 630; $^1$H-NMR (400 MHz, CDCl$_3$) δ/ppm: 3.52 (3H, s, CH$_2$OCH$_3$), 4.41 (2H, d, J=1.6 Hz, CH$_2$OCH$_3$), 7.28 (1H, td, J=7.6, 0.8 Hz, ArH), 7.34 (1H, d, J=8.4 Hz, ArH), 7.48-7.53 (2H, m, ArH), 7.78 (1H, t, J=1.6 Hz, H-4); $^{13}$C-NMR (100 MHz, CDCl$_3$) δ/ppm: 59.1, 69.0, 116.5, 119.2, 124.5, 126.0, 127.7, 131.1, 138.2, 153.1, 160.4; MS (EI) m/z: 190 (M$^+$, 2%), 175 (68%), 160 (100%), 103 (41%); Anal. calcd for C$_{11}$H$_{10}$O$_3$ (190.20): C, 69.46; H, 5.30. found: C, 69.21; H, 5.42.

3-Ethoxymethylcoumarin (F$_2$): (0.15 g, 73%); m.p.: 95-96° C., R$_f$=0.38 (ethyl acetate:n-Hexane=1:5); IR (KBr cm$^{-1}$): 2970, 2924, 2863, 2341, 1717, 1605, 1574, 1447, 1384, 1283, 1172, 1116, 1061, 919, 756, 630; $^1$H-NMR (400 MHz, CDCl$_3$) δ/ppm: 1.31 (3H, t, J=7.0 Hz, OCH$_2$CH$_3$), 3.68 (2H, q, J=7.0 Hz, OCH$_2$CH$_3$), 4.46 (2H, d, J=1.6 Hz, CH$_2$OCH$_2$CH$_3$), 7.28 (1H, td, J=7.6, 1.2 Hz, ArH), 7.34 (1H, d, J=8.0 Hz, ArH), 7.48-7.52 (2H, ArH), 7.81 (1H, t, J=1.6 Hz, H-4); $^{13}$C-NMR (100 MHz, CDCl$_3$) δ/ppm: 15.2, 66.9, 66.9, 116.5, 119.2, 124.4, 126.4, 127.7, 131.0, 138.1, 153.1, 160.5; MS (EI) m/z: 175 ([M-(C$_2$H$_5$)]$^+$, 53%), 160 (100%), 132 (51%), 131 (42%); Anal. calcd for C$_{12}$H$_{12}$O$_3$ (204.22): C, 70.57; H, 5.92. found: C, 70.60; H, 5.95.

3-Isopropoxymethylcoumarin (F$_3$): (0.16 g, 73%); R$_f$=0.46 (ethyl acetate:n-hexane=1:5), m.p.: 72-71° C., IR (KBr cm$^{-1}$): 2970, 1715, 1602, 1449, 1169, 1125, 1036, 917, 754, 630; $^1$H-NMR (400 MHz, CDCl$_3$) δ/ppm: 1.27 (6H, d, J=6.4 Hz, OCH(CH$_3$)$_2$), 3.78 (1H, hept, J=6.4 Hz, OCH(CH$_3$)$_2$), 4.45 (2H, d, J=1.6 Hz, CH$_2$OCH(CH$_3$)$_2$), 7.27 (1H, td, J=7.6, 0.8 Hz, ArH), 7.33 (1H, d, J=8.0 Hz, ArH), 7.47-7.52 (2H, m, ArH), 7.82 (1H, t, J=1.6 Hz, H-4); $^{13}$C-NMR (100 MHz, CDCl$_3$) δ/ppm: 22.1, 64.5, 72.4, 116.5, 119.3, 124.4, 127.0, 127.7, 130.9, 137.9, 153.0, 160.5; MS (EI) m/z: 175 ([M-(C$_3$H$_7$)]$^+$, 52%), 160 (100%), 159 (49%), 132 (45%); Anal. calcd for C$_{13}$H$_{14}$O$_3$ (218.25): C, 71.54; H, 6.47. found: C, 71.51; H, 6.45.

3-Butoxymethylcoumarin (F$_4$): (0.18 g, 77%); m.p.: 69-70° C., R$_f$=0.49, (ethyl acetate:n-hexane=1:5); IR (KBr cm$^{-1}$): 2924, 2854, 1717, 1637, 1456, 1385, 1282, 1170, 1144, 1114, 1055, 1018, 919, 756, 631; $^1$H-NMR (400 MHz, CDCl$_3$) δ/ppm: 0.96 (3H, t, J=7.4 Hz, OCH$_2$CH$_2$CH$_2$CH$_3$), 1.40-1.49 (2H, m, OCH$_2$CH$_2$CH$_2$CH$_3$), 1.63-1.70 (2H, m, OCH$_2$CH$_2$CH$_2$CH$_3$), 3.61 (2H, t, J=6.6 Hz, OCH$_2$CH$_2$CH$_2$CH$_3$), 4.45 (2H, d, J=1.6 Hz, CH$_2$OC$_4$H$_9$), 7.28 (1H, td, J=7.2, 0.8 Hz, ArH), 7.34 (1H, H, J=8.0 Hz, ArH), 7.47-7.52 (2H, m, ArH), 7.79 (1H, br s, H-4); $^{13}$C-NMR (100 MHz, CDCl$_3$) δ/ppm: 13.9, 19.3, 31.7, 67.1, 71.3, 116.5, 119.3, 124.4, 126.5, 127.7, 131.0, 138.0, 153.0, 160.5; MS (EI) m/z: 175 ([M-(C$_4$H$_9$)]$^+$, 37%), 160 (100%), 132 (53%); Anal. calcd for C$_{14}$H$_{16}$O$_3$ (232.28): C, 72.39; H, 6.94. found: C, 72.35; H, 6.95.

6-Chloro-3-ethoxymethylcoumarin (F$_5$): (0.18 g, 75%); R$_f$=0.45 (ethyl acetate:n-hexane=1:5), m.p.: 100-101° C.; IR (KBr cm$^{-1}$): 2972, 2861, 1729, 1637, 1605, 1570, 1478, 1379, 1266, 1172, 1124, 1055, 1014, 925, 826, 758, 659; $^1$H-NMR (400 MHz, CDCl$_3$) δ/ppm: 1.31 (3H, t, J=7.0 Hz, OCH$_2$CH$_3$), 3.68 (2H, q, J=7.0 Hz, OCH$_2$CH$_3$), 4.45 (2H, d, J=1.6 Hz, CH$_2$OCH$_2$CH$_3$), 7.28 (1H, d, J=8.8 Hz, H-8), 7.45 (2H, dd, J=8.8, 2.4 Hz, H-7), 7.50 (1H, d, J=2.4 Hz, H-5), 7.74 (1H, brs, H-4); $^{13}$C-NMR (100 MHz, CDCl$_3$) δ/ppm: 15.1, 66.8, 66.9, 117.9, 120.3, 126.9, 127.9, 129.7, 130.9, 136.7, 151.4, 159.8; MS (EI) m/z: 211 ([(M+2)-(C$_2$H$_5$)]$^+$, 14%), 209 ([M-(C$_2$H)]$^+$, 45%), 194 (100%), 166 (54%), 165 (41%); Anal. calcd for C$_{12}$H$_{11}$ClO$_3$ (238.67): C, 60.39; H, 4.65. found: C, 60.21; H, 4.64.

6-Bromo-3-ethoxymethylcoumarin (F$_6$): (0.20 g, 71%); m.p.: 118-119° C., R$_f$=0.48 (ethyl acetate:n-hexane=1:5); IR (KBr cm$^{-1}$): 2970, 2860, 1728, 1637, 1601, 1476, 1379, 1266, 1246, 1173, 1125, 1054, 1013, 923, 824, 759, 650; $^1$H-NMR (400 MHz, CDCl$_3$) δ/ppm: 1.31 (3H, t, J=7.0 Hz, OCH$_2$CH$_3$), 3.67 (2H, q, J=7.0 Hz, OCH$_2$CH$_3$), 4.45 (2H, d, J=1.6 Hz, CH$_2$OCH$_2$CH), 7.22 (1H, d, J=8.8 Hz, H-8), 7.58 (1H, dd, J=8.8, 2.4 Hz, H-7), 7.65 (1H, d, J=2.4 Hz, H-5), 7.73 (1H, t, J=1.6 Hz, H-4); $^{13}$C-NMR (100 MHz, CDCl$_3$) δ/ppm: 15.1, 66.8, 66.9, 117.0, 118.3, 120.8, 127.8, 130.0, 133.7, 136.6, 151.9, 159.8; MS (EI) m/z: 255 ([(M+2)-(C$_2$H$_5$)]$^+$, 34%), 253 ([M-(C$_2$H$_5$)]$^+$, 39%), 240 (95%), 239 (22%), 238 (100%), 212 (36%), 211 (33%), 210 (36%), 102 (63%); Anal. calcd for C$_{12}$H$_{11}$BrO$_3$ (283.12): C, 50.91; H, 3.92. found: C, 50.82; H, 3.92.

7-Benzyloxy-3-ethoxymethylcoumarin (F$_7$): (0.27 g, 87%); m.p.: 122-124° C., R$_f$=0.48 (ethyl acetate:n-hexane=1:6); IR (KBr cm$^{-1}$): 2976, 2923, 2858, 1714, 1620, 1388, 1245, 1163, 1132, 843, 724; $^1$H-NMR (400 MHz, CDCl$_3$) δ/ppm: 1.30 (3H, t, J=6.8 Hz, OCH$_2$CH$_3$), 3.66 (2H, q, J=6.8 Hz, OCH$_2$CH$_3$), 4.42 (2H, d, J=1.2 Hz, CH$_2$OCH$_2$CH$_3$), 5.11 (2H, s, OCH$_2$Ph), 6.88 (1H, d, J=2.4 Hz, H-8), 6.92 (1H, dd, J=8.8, 2.4 Hz, H-6), 7.33-7.45 (6H, m, H-5 and ArH), 7.73 (1H, br s, H-4); $^{13}$C-NMR (100 MHz, CDCl$_3$) δ/ppm: 15.1, 66.7, 66.9, 70.4, 101.6, 113.0, 113.2, 122.8, 127.5, 128.3, 128.6, 128.7, 135.8, 138.5, 154.7, 160.8, 161.3; MS (EI) m/z: 310 (M$^+$, 0.4%), 91 (100%); Anal. calcd. for C$_{19}$H$_{19}$O$_4$ (310.34): C, 73.53; H, 5.85. found: C, 73.49; H, 5.87.

7-Methoxy-3-ethoxymethyl-coumarin (F$_8$): (0.19 g, 81%); m.p.: 64-66° C., R$_f$=0.58 (ethyl acetate:n-hexane=1:3); IR (KBr cm$^{-1}$): 2975, 2909, 2874, 1726, 1624, 1390, 1151, 1121, 1022, 926, 823; $^1$H-NMR (400 MHz, CDCl$_3$) δ/ppm: 1.30 (3H, t, J=6.8 Hz, OCH$_2$CH$_3$), 3.67 (2H, q, J=6.8 Hz, OCH$_2$CH$_3$), 3.87 (3H, s, OCH$_3$), 4.43 (2H, d, J=1.6 Hz, CH$_2$OCH$_2$CH$_3$), 6.83 (1H, d, J=2.8 Hz, H-8), 6.85 (1H, dd, J=8.4, 2.8 Hz, H-6), 7.40 (1H, d, J=8.4 Hz, H-5) 7.74 (1H, t, J=1.6 Hz, H-4); $^{13}$C-NMR (100 MHz, CDCl$_3$) δ/ppm: 15.2, 55.7, 66.7, 67.0, 100.5, 112.6, 112.9, 122.7, 128.6, 138.6, 154.8, 160.9, 162.2; MS (EI) m/z: 234 (M$^+$, 1%), 205 ([M-(C$_2$H$_5$)]$^+$, 30%), 190 (100%), 162 (69%); Anal. calcd. for C$_{13}$H$_{14}$O$_4$ (234.25): C, 66.66; H, 6.02. found: C, 66.54; H, 6.00.

8-Methoxy-3-ethoxymethyl-coumarin (F$_9$): (0.20 g, 85%); m.p.: 131-133° C., R$_f$=0.51 (ethyl acetate:n-hexane=1:3); IR (KBr cm$^{-1}$): 2974, 2862, 1698, 1607, 1580, 1481, 1456, 1279, 1268, 1177, 1124, 1103, 1066, 914, 744; $^1$H-NMR (400 MHz, CDCl$_3$) δ/ppm: 1.31 (3H, t, J=6.8 Hz, OCH$_2$CH$_3$), 3.68 (2H, q, J=6.8 Hz, OCH$_2$CH$_3$), 3.97 (3H, s, OCH$_3$), 4.46 (2H, d, J=1.6 Hz, CH$_2$OCH$_2$CH$_3$), 7.05 and 7.09 (each 1H, dd, J=8.0, 1.2 Hz, H-5 and H-7), 7.21 (1H, t, J=8.0 Hz, H-6), 7.78 (1H, J=1.6 Hz, H-4); $^{13}$C-NMR (CDCl$_3$, 100 MHz) δ/ppm: 15.1, 56.2, 66.9, 112.9, 119.2, 119.9, 124.3, 126.7, 138.1, 142.7, 147.1, 159.9; MS (EI) m/z: 234 (M$^+$, 0.3%), 205 ([M-(C$_2$H$_5$)]$^+$, 31%), 190 (100%), 162 (39%); Anal. calcd. for C$_{13}$H$_{14}$O$_4$ (234.25): C, 66.66; H, 6.02. found: C, 66.61; H, 5.99.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for preparing a coumarin compound of formula (F), in which R$^1$, R$^2$, and R$^3$ are independently H, C$_1$~C$_7$ alkoxy, C$_1$~C$_7$ alkyl, phenoxy, benzyloxy, or a halogen atom; R$^4$ is an alkyl group; and Ar is an optionally substituted aryl group,

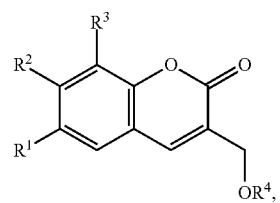

(F)

the method comprising: treating a chromene compound having the following formula (E)

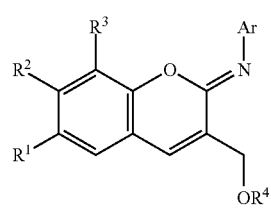

(E)

with an acid in the presence of water.

2. The method of claim 1, wherein R$^4$ is a C$_1$-C$_4$ alkyl group.

3. The method of claim 1, wherein Ar is unsubstituted aryl, haloaryl, alkylaryl, or alkoxyaryl.

4. The method of claim 3, wherein Ar is phenyl, halophenyl, alkoxyphenyl, or alkylphenyl.

5. The method of claim 4, wherein Ar is phenyl, 4-fluoro-phenyl, 4-chloro-phenyl, 4-bromo-phenyl, 4-methyl-phenyl, 4-methoxy-phenyl or 3-methoxy-phenyl.

6. The method of claim 2, wherein R$^1$, R$^2$, and R$^3$ are independently H, Cl, Br, benzyloxy, or methoxy; and R$^4$ is methyl, ethyl, i-propyl, or n-butyl.

7. The method of claim 1, wherein the acid is selected from the group consisting of HCl, HBr, HI, CH$_3$CO$_2$H, and combinations thereof.

* * * * *